(12) United States Patent
Helbert et al.

(10) Patent No.: US 6,426,189 B1
(45) Date of Patent: Jul. 30, 2002

(54) CELLULOSE FILMS FOR SCREENING

(75) Inventors: William Helbert, Roscoff; Henri Dominique Chanzy, La Tronche, both of (FR); Steffen Ernst, Kobenhavn N (DK); Martin Schulein, Copenhagen O (DK); Tommy Lykke Husum, Hillerod (DK); Lars Kongsbak, Holte (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/676,713

(22) Filed: Sep. 29, 2000

Related U.S. Application Data
(60) Provisional application No. 60/157,912, filed on Oct. 6, 1999.

(30) Foreign Application Priority Data

Oct. 1, 1999 (DK) .......................................... 1999 01414

(51) Int. Cl.$^7$ ................................................. C12Q 1/68
(52) U.S. Cl. ............................ 435/6; 435/18; 435/69.1; 435/209
(58) Field of Search .............................. 435/6, 18, 209, 435/69.1

(56) References Cited

U.S. PATENT DOCUMENTS

| | | |
|---|---|---|
| 4,861,427 A | 8/1989 | Johnson et al. |
| 4,863,565 A | 9/1989 | Johnson et al. |
| 5,585,273 A | 12/1996 | Lawrence et al. ........ 435/288.7 |
| 6,063,611 A * | 5/2000 | Van Solingen ............. 435/209 |

FOREIGN PATENT DOCUMENTS

| | | |
|---|---|---|
| JP | 10095803 | 4/1998 |
| WO | WO 89/12107 | 12/1989 |
| WO | WO 93/11182 | 6/1993 |
| WO | WO 97/11193 | 3/1997 |
| WO | WO 99/34011 | 7/1999 |
| WO | WO 99/45143 | 9/1999 |

OTHER PUBLICATIONS

WPI accession No. 1984–021105.

Abstract JP 49060289.

Abstract JP 58202000.

* cited by examiner

Primary Examiner—James Ketter
(74) Attorney, Agent, or Firm—Elias Lambiris; Jason Garbell

(57) ABSTRACT

The invention relates to a cellulose film comprising microfibrillated cellulose and to the use of it for screening of a biological compound and nucleic acids encoding a biological compound.

19 Claims, 12 Drawing Sheets

CELLULOSE FILMS FOR SCREENING

CROSS-REFERENCE TO RELATED APPLICATIONS

This application claims priority under 35 U.S.C. 119 of Danish application PA 1999 01414 filed on Oct. 1, 1999 and U.S. provisional application No. 60/157,912 filed on Oct. 6, 1999, the contents of which are fully incorporated herein by reference.

TECHNICAL FIELD

This invention relates to cellulose films and to methods for their use for identifying or screening actives such as biological compounds or nucleic acid sequences encoding such. Also the invention relates biological compounds found or identified by these methods and to methods of producing biological compounds identified.

BACKGROUND

The art of identifying useful biological compounds in unknown samples or compositions, such as enzymes, encompasses disclosures such as WO 99/34011 disclosing use of textile test swatches for identifying enzymes. EP 454 046 B1 discloses a test slide for detecting the presence of micro-organisms, their enzymes and metabolites. JP 49060289 A discloses an enzyme activity test disk for detection of enzyme activities in the digestive tract.

Bacterial cellulose is described e.g. in disclosures such as U.S. Pat. No. 4,863,565; WO 93/11182 and U.S. Pat. No. 4,861,427.

JP10-95803 discloses bacterial cellulose coatings e.g. for paper.

SUMMARY OF THE INVENTION

Figure 1:
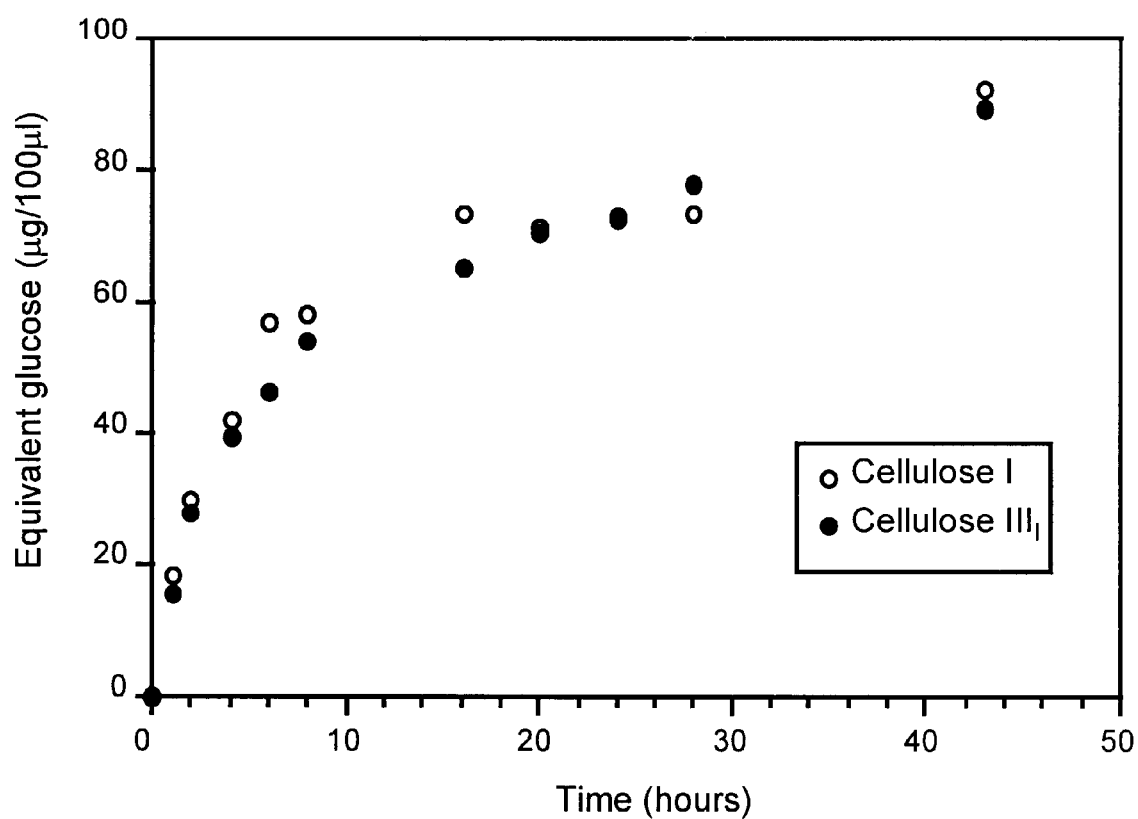
FIG. 1 shows degradation of bacterial Cellulose I and Cellulose III$_I$ by H. insolens complex.

The present invention relates to a method for screening of an active such as a biological compound or a nucleic acid sequence encoding a biological compound using a cellulose film comprising microfibrillated cellulose. Specifically the invention provides a method for screening or identifying a an active, preferably a biological compound, comprising contacting a sample containing the active with a cellulose film comprising microfibrillated cellulose and detecting an interaction between the cellulose film and the active.

The invention also relates to cellulose films and processes for their manufacture which are suitable for the screening method. Specifically the invention provides a cellulose film comprising microfibrillated cellulose, wherein the film further comprises a substance attached to the microfibrillated cellulose.

Further the invention relates to test containers comprising a cellulose film and processes for their manufacture, which are suitable for carrying out the screening process. Specifically the invention provides a container, preferably having a volume of less than 10 ml, comprising at least one surface coated with a cellulose film.

Still further, the invention relates to an active, preferably a biological compound identified by the screening method as well as processes for their manufacture. Specifically the invention provides an active, preferably a biological compound and/or a nucleic acid sequence encoding a biological compound identified by the screening process

DETAILED DESCRIPTION OF THE INVENTION

One object of the present invention is to provide improved methods for finding new cleaning materials, such as enzymes. In finding new materials suitable for cleaning e.g. cellulose containing fabrics one may chooses to test the new materials on real fabrics to determine if they possess any cleaning properties. However, this approach is undesirable because of the slowness and limited capacity of such methods. Accordingly another object of the invention is to provide improved methods capable of testing large numbers of potential candidates at a considerable speed. Further objects are to provide methods which can be carried out on small samples and which may be easily automated.

Definitions

The term "microfibrillated cellulose" as used herein is to be understood as isolated and purified cellulose fibres recovered from a source in a process preserving the original cellulose filamentous structure. Microfibrillated cellulose will hereafter be denoted "MFC". Also encompassed by the this term are cellulose fibres, which after isolation and purification has undergone chemical treatment changing the internal structure and/or arrangement of the fibres. Consequently the term microfibrillated cellulose encompass purified and isolated cellulose from microorganisms such as bacterial cellulose (hereinafter denoted "BC").

In context of the invention, the term "nucleic acid source" is to be understood as any DNA, RNA or cDNA material or material comprising DNA, RNA or cDNA.

In the context of the invention, the term expression system is to be understood as a system enabling transcription of a nucleic acid sequence and translation into the synthesis of the corresponding biological compound. The expression system may be a cell or an in vitro system.

In the context of the invention, the term gene library is to be understood as fragments of DNA or cDNA derived from a nucleic acid source.

In the context of the invention, the term "host cell" is to be understood as a cell, which may host and may express an inserted DNA or cDNA fragment from a gene library.

In the context of the invention, the term "transformant" or "transformed host cell" is to be understood as a host cell in which a DNA or a cDNA fragment from a gene library has been inserted.

In the context of the invention, the term "clone" is to be understood as a copy of a cell or a transformed host cell.

The term "active" as used herein is to be understood any compound or a mixture of compounds, which perform a measurable interaction with a cellulose film and/or any substance incorporated in or associated to a cellulose film.

Microfibrillated cellulose

The cellulose film of the invention comprises MFC. We have found that such cellulose films mimics cellulose containing textile surprisingly well and may advantageously substitute such textile or fabric when screening for actives, preferably biological compounds, interacting with cellulose in textile or substances present on a textile surface. This is an important aspect because when searching for new cleaning agents e.g. biological compounds such as enzymes, and testing their effect on a cellulose film mimicking a real textile it is more likely that found candidates will also work well on real textile. Choosing more artificial test conditions, however, may generate a large number of false candidates in the screening, i.e. enzymes may be found which works well under artificial conditions, but will perform poorly on real textile.

MFC also possesses an enhanced accessibility towards e.g. cellulase enzymes which may reacts more readily with MFC than with cellulose which has not been microfibrillated. The enhanced accessibility of MFC also means the MFC is easier penetrated by water. The enhanced accessibility further means that the MFC may be easier modified e.g. by reacting compounds onto the MFC by e.g. esterification, etherification, sulfonation, phosporylation and/or carboxylation.

Accordingly a cellulose film of the invention may used to identify cleaning agent, such as enzymes, which will also have good cleaning properties Moreover an important feature of the cellulose film of the invention is that it is possible to prepare such cellulose film in very small containers, such as wells in a conventional micro plate. Especially for micro plates containing very small wells such as 96, 384 or 1536 well plates with corresponding well volumes of 320 $\mu$l, 160 $\mu$l, and 14 $\mu$l, respectively, it is very difficult to use pieces of real textile.

MFC is a form of expanded high volume cellulose, in which cellulose fibres are opened up and unraveled to expose smaller fibrils and microfibrils. The fibrils of the MFC in a film of the invention have an average length of about at least 10 $\mu$m, preferably about at least 50 $\mu$m, most preferably about at least 100 $\mu$m. However a preferred average length of the fibrils is less than about 500 $\mu$l, more preferably less than about 300 $\mu$l, most preferably less than about 200 $\mu$l. The average width of the fibrils are between about 50–200 nm, preferably about 75–150 nm, most preferably about 80–120 nm. Each fibril consists of a bundle of microfibrils. The microfibrils in the fibrils have an average thickness of about 2–20 nm preferably about 5 nm and each fibril contains a bundle of about 50–100 microfibrils. The isolated and purified fibrils are surprisingly long. In the microfibrils the native Cellulose I internal structure is preferably retained, so that the polymeric chains of glucose monomers constituting each cellulose chain are arranged parallel to each other. However, internal structures obtained by chemical modification of the original structure, by methods known to the art, are also preferred such as a Cellulose II structure in which the cellulose chains are arranged antiparallel to each other or a Cellulose III structure in which the hydrogen bonding of the Cellulose I structure is altered or a Cellulose IV structure.

Sources of Cellulose

The MFC comprised in the film of the invention may be obtained from any suitable source. Such as microorganisms producing cellulose or from plants such as wood (e.g. soft wood or pulped soft wood), cotton, straw, jute, grasses, tunicate or cereals such as bran. However, a source is preferred in which the cellulose in the source is available in way so that MFC may be isolated and purified in a way to preserve long fibrils or microfibrils. Accordingly preferred cellulose sources are microorganisms and cotton. Preferred microbial cellulose is bacterial cellulose. Bacterial cellulose contains very long cellulose chains and/or fibers and has shown very good film forming properties. Such bacterial cellulose is also commercially available, e.g. from the product Nata de Coco, which is a fermented product of coconut milk, from Fujico Company, Kobe, Japan. This product contains bacterial cellulose produced during the fermentation process. A method for producing bacterial cellulose can also be found in JP10–95803.

Isolating, Purifying and Microfibrillating Cellulose

An example of preparing MFC from pulp of soft wood is known from Franklin W. et al; *Microfibrillated Cellulose: Morphology and Accessibility*; Journal of applied Polymer Science; 1983; Applied Polymer symposium 37; pp. 797–813; John Wiley & Sons, Inc. The preparation method is described on page 798 in the section "Preparation of microfibrillated cellulose" hereby incorporated by reference, and is further described on page 803 under "Discussion" in the section "Preparation of microfibrillated cellulose" also incorporated herein by reference. Also in EP 726 356 is a method for obtaining MFC described.

However, when isolating, purifying and microfibrillating cellulose useful for preparing a film which is suitable for substituting and/or mimicking a cellulose containing textile in a screening process it is preferred to employ methods and sources for which it is possible to obtain a long cellulose fibril structure, i.e. by avoiding breakage of the glucose chains constituting the cellulose and substantially preserving the original amounts of glucose units in the glucose chains. The method should deploy force to the cellulose fibres preferably only to expose the fibrils and microfibrils. The term substantially in this context means that the DP (degree of polymerisation) of the glucose chains should be lowered by no more than 500 glucose units from the original chain, preferably by no more than 350, more preferably by no more than 250 and most preferably by no more than 150 glucose units by the microfibrillation process.

A preferred cellulose is bacterial cellulose, which makes an excellent cellulose starting material for microfibrillation. Methods for obtaining cellulose from bacteria are known and described, such as from strains of Acetobacter described in U.S. Pat. No. 4,863,565 examples VI and VII, incorporated herein by reference.

Microfibrillation of a bacterial cellulose, such as from the product "nata de coco" may be achieved by washing the cellulose in plenty of water to remove water soluble impurities, treating the washed cellulose with an alkaline solution, such a NaOH and neutralising and blending the alkali treated cellulose to obtain a suspension of MFC.

Cellulose Films

The invention relates to a cellulose film comprising MFC. The film of the invention comprises preferably at least 50% w/w MFC, more preferably at least 75% w/w, more preferably at least 95% w/w and most preferably the film consist of substantially pure MFC. By using the term substantially it meant that small amounts of impurities originating from the source or from the purification or microfibrillation process may remain in the film, but no substances has intently or deliberately been added to the film. A preferred film comprises MFC substantially having a native Cellulose I structure, meaning that a major portion of the cellulose have a Cellulose I structure. Another preferred film comprises MFC substantially having a Cellulose II structure, while further preferred films comprise cellulose substantially having Cellulose III or Cellulose IV structures. Modification of cellulose structure is known to the art. The conversion of Cellulose I to Cellulose III is for example described in Chanzy et al.; *Structural changes of cellulose crystals during the reversible transformation cellulose I to cellulose III*; Valonia. Holzforschung; 40; suppl. 25–30. Interactions between MFC and e.g. different endoglucanase enzymes was found to be highly dependent on the cellulose structure.

The film have a preferred dry average thickness of about 10 μm to about 100 μm, more preferably about 20 μm to about 70 μm and most preferably about 30 μm to about 60 μm.

Modified Cellulose Films

Because the cellulose film comprises MFC the accessibility of the cellulose is enhanced. Accordingly the cellulose in the film may be reacted and/or attached and/or blended/mixed with one or more compounds or substances before or after formation of the film. Accordingly, in a preferred embodiment the cellulose film further comprises a compound or substance which before or after formation of the film has been reacted or attached or mixed with the MFC. Preferably the substance or compound is reacted and/or attached onto the surface of the film after formation of the film. The compound or substance may be attached to the MFC by covalent bonds or by ionic bonds or by hydrogen bonds such as by hydrophobic interaction between the compound or substance and the MFC or it may be mixed with the MFC before formation of the film, so that the substance or compound is embedded in a MFC matrix. Preferred compounds which may be attached to the MFC are compounds which possess optical or radioactive properties (often called markers or label agents) or which upon release or attachments to the film gains optical properties or may react with optically detective indicators. Compounds which possess optical properties or gain such properties may be reflectants or absorbants, such as particles of pigments reflecting or absorbing multi-wavelength light or more preferably dyes such as fluorescent dyes or light absorbing dyes, which emits or absorbs light at discrete wavelengths. Examples of reflectants are indigo, opaque agents, carbon black and/or titandioxide pigments. The dyes are typically conjugated organic molecules in which the conjugated system preferably is changed and the molecule either gain or loose fluorescence or absorbing properties when reacted to or released from the film. However dyes for which the conjugated system does not change may also be used. Fluorescent dyes, such as DTAF, fluorescein, Fluorescein-isothiocyanate—Isomer I, or fluorescein-5-thiosemicarbazide are preferred.

Among the dyes suitable for labelling cellulose, derivatives of cyanur chloride are preferred because it has been found possible to react them to cellulose. In a method for labelling cellulose with derivatives of cyanur chloride it has also been found the pH in the reaction medium is crucial for obtaining satisfactory labelling. Accordingly we have developed a method for labelling cellulose comprising reacting a derivative of cyanur chloride onto the cellulose at a pH between 9–10.

Other for attaching dyes to polysaccharides are known to the art and may be found e.g. in WO 99/45143 incorporated herein by reference.

Radioactive compounds encompasses all compounds comprising radioactive isotopes such as $S^{35}$, $P^{32}$, $H^3$ and/or $I^{125}$.

In a preferred embodiment the compound is a non-cellulose substrate for a non-cellulytic enzyme or a non MFC substrate, preferably comprising a moiety which possesses optical or radioactive properties as described, supra. The non-cellulytic enzyme substrate is preferably selected from amino acids, peptides, proteins, carbohydrate polymers, oligomers or monomers, fatty acids, fatty acid esters, fatty acid ester alcohols and triglycerides. Accordingly the substrate may a polysaccharide such as starch and/or a protein and/or a lipid.

Among dyes suitable for labelling acid groups, optically active derivatives of semithiocarbazid are preferred.

Among dyes suitable for labelling amine groups, optically active derivatives of isothioncyanate are preferred.

Also combinations of substrates are encompassed by the invention. Accordingly one useful combination is the combination of a cellulose film labelled with one dye mixed with a substantially amorphous cellulose such as CMC or PASC labelled with another dye. The term substantially in the context means that a major portion of the cellulose is in an amorphous form. When contacting such a film with an unknown cellulytic enzyme it may be identified if the enzyme mainly reacts with the amorphous cellulose or the crystalline MFC by detecting which dye is released from the film.

The compound may also be a staining substance, i.e. the cellulose film may be stained with a substance, preferably containing a protein or a lipid, fat or fatty acid or a polysaccharide or a naturally occurring colorant or combinations thereof. As examples the stain may be made of tomato ketchup, grass, coffee, tea or animal lard.

Preparation of Cellulose Films

The invention also relates to a method for preparing a cellulose film comprising MFC comprising preparing a suspension of MFC and sedimentation of the MFC as a film onto a surface.

The surface may be any surface which is substantially impermeable to the MFC, i.e. the surface is impermeable to a major part of the MFC. The surface may be of any suitable material such as stainless steel alloys, plastics/synthetic polymers, rubber, board, glass, wood, paper, textile, concrete, rock, marble, gypsum and ceramic materials which optionally may be coated, e.g. with paint, enamel, polymers and the like. The surface may however also be of biological origin such as mucous membranes, skin, teeth, hair, nails etc.

In a preferred embodiment the film is prepared by preparing a suspension of MFC in a container and sedimenting the MFC on at least one inner surface of the container, preferably the bottom surface of the container. The bottom surface of the container is preferably made of a synthetic polymer such as a plastic, and may optionally be translucent. Accordingly in a most preferred embodiment the container is a well in a microtiter plate, and preferably the microtiter plate contains 96 well or more such as 384 well or 1536.

Accordingly the container preferably have a volume of less than 10 ml, more preferably less than 1 ml, more preferably less than 500 µl, more preferably less than 300 µl, more preferably less than 50 µl and most preferably less than 15 µl. By employing such small containers film having a very small diameter may be prepared which is useful in a screening process. In order to sediment MFC, substantially having a cellulose I structure, on a surface from a suspension the concentration of MFC in an aqueous suspension should be less than 10 mg/ml suspension, preferably less than 2 mg/ml, more preferably less than 1 mg/ml and most preferably less than 0.7 mg/ml. For other cellulose structures these concentration may be higher, such as multiplied by two. The film should preferably stick or adhere to the surface and accordingly when preparing a film in container of dimensions corresponding to a well of a 96 well microtiter plate the total amount of MFC sedimented and dried on the bottom surface should not exceed 250 µg, preferably not exceed 200 µg and most preferably not exceed 150 µg. In such a container the best films are obtained by using about a 100 µl suspension with a concentration of MFC of 1 mg/ml or less. An important feature of the invention is that cellulose films of the invention may easily be reproducibly prepared in a vast number of identical containers such as wells in a microtiter plate.

Applications of Cellulose Films

The invention also relates to the use of a cellulose film of the invention for screening of actives, preferably biologically active compounds, such as enzymes. Because the film can be prepared reproducibly and used in a vast number very small containers and mimics cellulose containing textile or fabric it is very useful for detecting actives, such as enzymes, which interacts with the cellulose or compounds or substances attached to the cellulose.

Screening/identifying Actives

Most often screening for an active of interest requires contacting the active with a substance which will undergo a detectable change upon reaction and/or interaction with the active. For actives such as enzymes, the skilled person will usually have a range of such substances to choose from, but there is a desire to choose substances which resembles substances with which the enzyme will react in an intended real life industrial application. For enzymes, choosing a real type substrate to which an interesting enzyme has a high specificity in the screening process one advantage is that new enzymes found in the screening process also are very likely to work well in the intended industrial application. Choosing e.g. a low molecular synthetic substrate of low specificity instead, however, may generate a large number of false positive hits in a screening, i.e. enzymes may be found which reacts well with the synthetic substrate, but will perform poorly on the real substrate in the intended industrial application. By employing the cellulose film of the invention a real life application is mimicked and enzymes found by a screening method employing the cellulose film of the invention are likely to interact with real textile cellulose in a desired way.

Accordingly the invention provides a method for screening for an active, preferably a biological compound comprising contacting, preferably in an aqueous medium, a sample containing the active with a cellulose film comprising MFC and detecting an interaction between the cellulose film and the active.

In a preferred embodiment the method comprises the steps of:
(a) depositing a cellulose film of the invention on at least one inner surface of a container, preferably the bottom surface of a container having a volume of less than 10 ml,
(b) adding the active dissolved or dispersed in a, preferably aqueous, liquid to the film,
(c) incubating the film with the active and
(d) monitoring the interaction between the biological compound and the cellulose film, preferably by measuring a compound which have been released from the film by the interaction.

The released compound may in accordance with the invention be a dye, preferably fluorescent, or a radioactive compound or it may preferably be a product of a substrate labelled with a dye or a radioactive compounds which have reacted with the biological compound.

The active is preferably a selected from biological compound such as an enzyme and organic and inorganic detersive compounds. Relevant detersive compounds may be enzyme stabilizers, inhibitors, enhancers, co-factors, builders, builder systems, bleach systems, bleach activators, metal-containing bleach catalyst, optical brighteners, nonionic-, anionic-, cationic-, zwitterionic and amphoteric surfactants, fabric softening agents, softening clays, clay flocculants, dye-transfer inhibiting agents, polymeric soil release agents, clay soil removal agents, anti-soil redeposition agents, polymeric dispersing systems, chelating agents, alkoxylated polycarboxylates, carrier systems, dyes and pigments, fabric care agents, color care agents and like.

A preferred active is an enzyme. The enzyme may be a cellulose degrading or synthesising enzyme which interacts directly with the cellulose in the film and the presence of such enzymes may be detected by measuring the release of glucose oligo- or monomers from the film or the consumption of glucose oligo- or monomers from the medium in which the interaction occurs. Methods for detecting glucose oligo- or monomers are known to the art, e.g. from Kidby D. K. and Davidson d. J.; *A convenient ferricyanide estimation of reducing sugar in the nanomole range*; Analytical Biochemistry; 1973; 55; pp. 321–325. Such enzymes may be endoglucanases or cellulases such as those belonging to the group endo-1,4-beta-glucanase (EC 3.2.1.4) or endo-1,3(4)-β-glucanases (EC 3.2.1.6).

The enzyme classification employed is in accordance with *Recommendations* (1992) *of the Nomenclature Committee of the International Union of Biochemistry and Molecular Biology*, Academic Press, Inc., 1992.

The enzyme may equally preferred be a non-cellulose degrading enzyme which interacts with a substrate attached to the film or which isomerize cellulose. It is to be understood that enzyme variants (produced, for example, by recombinant techniques) are included within the meaning of the term "enzyme".

Accordingly the types of enzymes which may appropriately be screened include oxidoreductases (EC 1.-.-.-), transferases (EC 2.-.-.-), hydrolases (EC 3.-.-.-), lyases (EC 4.-.-.-), isomerases (EC 5.-.-.-) and ligases (EC 6.-.-.-).

Preferred oxidoreductases in the context of the invention are peroxidases (EC 1.11.1), laccases (EC 1.10.3.2) and glucose oxidases (EC 1.1.3.4)].

Preferred transferases are transferases in any of the following sub-classes:
a) Transferases transferring one-carbon groups (EC 2.1);
b) transferases transferring aldehyde or ketone residues (EC 2.2); acyltransferases (EC 2.3);
c) glycosyltransferases (EC 2.4);
d) transferases transferring alkyl or aryl groups, other that methyl groups (EC 2.5); and
e) transferases transferring nitrogeneous groups (EC 2.6).

A most preferred type of transferase in the context of the invention is a transglutaminase (protein-glutamine γ-glutamyltransferase; EC 2.3.2.13).

Preferred hydrolases in the context of the invention are: Carboxylic ester hydrolases (EC 3.1.1.-) such as lipases (EC 3.1.1.3); phytases (EC 3.1.3.-), e.g. 3-phytases (EC 3.1.3.8) and 6-phytases (EC 3.1.3.26); glycosidases (EC 3.2, which fall within a group denoted herein as "carbohydrases"), such as α-amylases (EC 3.2.1.1); peptidases (EC 3.4, also known as proteases); and other carbonyl hydrolases].

In the present context, the term "carbohydrase" is used to denote not only enzymes capable of breaking down non-cellulose carbohydrate chains (e.g. starches) of especially five- and six-membered ring structures (i.e. glycosidases, EC 3.2), but also enzymes capable of isomerizing carbohydrates, e.g. six-membered ring structures such as D-glucose to five-membered ring structures such as D-fructose.

Carbohydrases of relevance include the following (EC numbers in parentheses):

α-amylases (EC 3.2.1.1), β-amylases (EC 3.2.1.2), glucan 1,4-α-glucosidases (EC 3.2.1.3), , endo-1,4-β-xylanases (EC 3.2.1.8), dextranases (EC 3.2.1.11), chitinases (EC 3.2.1.14), polygalacturonases (EC 3.2.1.15), lysozymes (EC 3.2.1.17), β-glucosidases (EC 3.2.1.21), α-galactosidases (EC 3.2.1.22), β-galactosidases (EC 3.2.1.23), amylo-1,6-glucosidases (EC 3.2.1.33), xylan 1,4-β-xylosidases (EC 3.2.1.37), glucan endo-1,3-β-D-glucosidases (EC 3.2.1.39), α-dextrin endo-1,6-α-glucosidases (EC3.2.1.41), sucrose α-glucosidases (EC 3.2.1.48), glucan endo-1,3-α-glucosidases (EC 3.2.1.59), glucan 1,4-β-glucosidases (EC 3.2.1.74), glucan endo-1,6-β-glucosidases (EC 3.2.1.75), arabinan endo-1,5-α-L-arabinosidases (EC 3.2.1.99), lactases (EC 3.2.1.108), chitosanases (EC 3.2.1.132) and xylose isomerases (EC 5.3.1.5).

The invention also relates to a biological compound identified the method of the invention.

The sample to be screened may contain the active in a crude or a purified form or it may in case the active is a biological compound contain cells or in vitro coupled transcription and translation system which produce or have produced the biological compound. The cells may be bacterial cells, archaeal cells and/or eucaryotic cells.

In a preferred embodiment the active is an enzyme in a detergent composition. It is known to the art that enzyme properties such as activity and stability may be altered or inactivated by the presence of detergents. Accordingly it is desired to screen for an enzyme in the presence of a detergent because enzymes which are more effective in detergent compositions may be identified. Accordingly the screening method of the invention may advantageously replace such screening methods known to the art e.g. as described in WO 99/34011.

Screening For Nucleic Acid Sequences

As biological compounds, which can be screened and detected by the method of the invention may be expressed by a cell or an in vitro system encoded by nucleic acid sequences comprised in the cell or in vitro system, also nucleic acid sequences encoding a biological compound may be screened and identified and isolated.

Accordingly the invention also provides a method for screening a nucleic acid sequence encoding a biological compound, wherein the method comprises:

(a) expressing a nucleic acid sequence in an expression system, so as to produce a biological compound, (b) contacting the biological compound with a cellulose film preferably comprising MFC, c) measuring an interaction between the biological compound and the cellulose film and d) selecting expression systems for which a detectable interaction occurred and recovering the nucleic acid sequence.

Nucleic Acid Sequence Sources

The nucleic acid sequence originates from a source. In a preferred embodiment of the invention the source of the nucleic acid the be screened is a cell, e.g. a prokaryotic cell, an archaeal cell or an eucaryotic cell. The cell may further have been modified by genetic engineering. A preferred bacterial cell is of the genus Bacillus, e.g. *B. licheniformis*, while a preferred eucaryotic cell is a mammal cell, e.g. a human cell, a plant cell, e.g. *Arabidopsis thaliana* or a fungus, e.g. *Meribipilus gigantus*.

In another preferred embodiment the nucleic acid source is a mixed population of cells. The DNA or RNA of the cells may further be extracted, as described vide infra, directly from any biotic or abiotic sample, e.g. a soil sample, a water sample, or a rumen sample. Also preferred nucleic acid sources are cells of extremeophile prokaryotics, such as thermophiles.

The nucleic acid source may also be cells which have been subjected to classical mutagenesis, e.g. by UV irradiation of the cells or treatment of cells with chemical mutagens as described by Eisenstadt E., Carlton B. C. and Brown B. J., *Gene mutation*, Methods for general and molecular bacteriology, pp. 297–316, Eds: Gerhardt P., Murray R. G. E., Wood W. A. and Krieg N. R., ASM, 1994.

Further the nucleic acid source may be a population of cells genetically modified by in vivo gene shuffling as described in WO 97/07205.

In a further preferred embodiment the nucleic acid source is in vitro made preparations of sequences of DNA, RNA, cDNA or artificial genes obtainable by e.g. gene shuffling (e.g. described by Stemmer, Nature, 370, pp. 389–391, 1994 or Stemmer, Proc. Natl. Acad. Sci. USA, 91, pp. 10747–10751, 1994 or Wo 95/17413), random mutagenesis (e.g. described by Eisenstadt E., Carlton B. C. and Brown B. J., *Gene mutation*, Methods for general and molecular bacteriology, pp. 297–316, Eds: Gerhardt P., Murray R. G. E., Wood W. A. and Krieg N. R., ASM, 1994) or constructed by use of PCR techniques (e.g. described by Poulsen L. K., Refn A., Molin S. and Andersson P., Topographic analysis of the toxic Gef protein from *Escherichia coli*, Molecular Microbiology, 5(7), pp.1627–1637, 1991)

Expression Systems

In the method of the invention nucleic acid sequences to be screened are expressed in an expression system. The expression system is a system enabling transcription of a nucleic acid sequence and translation into the synthesis of the corresponding biological compound. The expression system may be cellular or an in vitro system. A description of in vitro coupled transcription and translation may be found in Ohuchi, S. et al.; *In vitro method for generation of protein libraries using PCR amplification of a single DNA molecule and coupled transcription/translation*; Nucleic Acid research, 1998, vol. 26. No. 19, pp. 4339–4346 or Ellman J., Mendel D., Anthony-Cahill S. J., Noren C. J. and Schultz P. G., Methods in Enzymol.1991; vol. 202; pp. 301–337, enabling expression of a nucleic acid sequence, e.g. a gene library derived from a nucleic acid source. In the case of a cellular expression system, the cell may be the nucleic acid sequence source itself, e.g. a wild type cell isolated from nature, or it may be a cell from a population of transformed host cells or clones thereof comprising a gene library prepared from a nucleic acid source according to methods known to the art (e.g. described vide infra).

Host Cells

The host cell according to the definition may be any cell able of hosting and expressing a nucleic acid fragment from a gene library.

A preferred host cell does not in itself contain or express nucleic acid sequences encoding for biological compounds (i.e. untransformed host cells are unable of significantly expressing the biological compound), which will interfere with the screening method. This cell characteristic may either be a natural feature of the cell or it may be obtained by deletion of such sequences as described e.g. in Christiansen L. C., Schou S., Nygaard P. and Saxild H. H., Xanthine metabolism in Bacillus subtilis: Characterization of the xpt-pbux operon and evidence for purine and nitrogen controlled expression of genes involved in xanthine salvage and catabolism, Journal of Bacteriology, 179(8), pp 2540–2550, 1997 or Stoss O., Mogk A. and Schumann W., Integrative vector for constructing single copy translational fusions between regulatory regions of Bacillus subtilis and the bgaB reporter gene encoding a heat stable beta-galactosidase, FEMS Microbiology Letters, 150(1), pp 49–54, 1997.

In another preferred embodiment of the invention the host cell is a bacterial cell or an eucaryotic cell. Further the bacterial cell is preferably a ElectroMAX DH10B (GibcoBRL/Life technologies, UK)cell or of the genus E. coli, e.g. SJ2 E. coli of Diderichsen, B., Wedsted, U., Hedegaard, L., Jensen, B. R., Sjoholm, C., "Cloning of aldB, which encodes alpha-acetolactate decarboxylase, an exoenzyme from Bacillus brevis", J. Bacteriol., 172, pp 4315–4321, 1990. Other preferred host cells may be strains of Bacillus, such as Bacillus subtilis or Bacillus sp. A preferred eucaryotic cell is preferably a yeast, e.g. S. cerevisae.

Preparation of Gene Libraries

Preparation of a gene library can be achieved by use of known methods.

Procedures for extracting DNA from a cellular nucleic acid source and preparing a gene library are described in e.g. Pitcher, D. G., Saunders, N. A., Owen, R. J., "Rapid extraction of bacterial genomic DNA with guanidium thiocyanate", Lett. Appl. Microbiol., 8, pp 151–156, 1989 or Dretzen, G., Bellard, M., Sassone-Corsi, P., Chambon, P., "A reliable method for the recovery of DNA fragments from agarose and acryla-mide gels", Anal. Biochem., 112, pp 295–298, 1981 or WO 94/19454 or Diderichsen et al., supra.

Procedures for preparing a gene library from an in vitro made synthetic nucleic acid source can be found in (e.g. described by Stemmer, supra or WO 95/17413).

Insertion of Gene Libraries Into Host Cells

Procedures for transformation of a host cell by insertion of a plasmid comprising a DNA or cDNA fragment from a gene library is well known to the art, e.g. Sambrook et al., "Molecular cloning: A laboratory manual", Cold Spring Harbor lab., Cold Spring Harbor, N.Y.; 1989 or Ausubel, F. M. et al. (eds.) Current protocols in Molecular Biology, John Wiley and Sons, 1995 and Harwood, C. R., and Cutting, S. M. (eds.), "Molecular Biological Methods for Bacillus", John Wiley and Sons, 1990.

In a preferred embodiment of the invention the plasmid to be inserted into a host cell also contains a nucleic acid sequence (denoted as an antibiotic marker), which may enable resistance of a transformant to an antibacterial or antifungal agent e.g. an antibiotic. Resistance to chloramphenicol, tetracycline, kanamycin, ampicillin, erythromycin or zeocin is preferred.

In a further preferred embodiment of the invention the pSJ1678 plasmid DNA of WO 94/19454 and Diderichsen et al. (1990), supra, which enables resistance to chloramphenicol, may be used for transforming a SJ2 E. coli host cell. Alternatively the plasmid pZErO-2 (Invitrogen, CA, USA) may be used).

Screening Procedures

In the case of an in vitro expression system as a specific embodiment of the invention the screening procedure preferably comprises:

a) preparing a gene library from a nucleic acid source, b) separating the gene fragments of the library into separate containers.

c) amplifying the separated gene fragments, d) performing in vitro coupled transcription/translation of the amplified gene fragments so as to express a biological compound.

e) contacting the biological compound in each separate container or subsamples thereof with a cellulose film of the invention, f) incubating the biological compound with the cellulose film, g) detecting an interaction between the cellulose film and the biological compound, h) recovering gene fragments in containers in which an interaction has occurred Steps a–h may suitably be achieved by use of commercially available standard equipment such as pipettes or automated pipette equipment, flasks, microtiter plates, shakers, thermostated incubators etc.

An interaction between a biological compound and the cellulose film occurs only in containers containing and expressing a gene fragment or nucleic acid sequence encoding for a biological compound.

The separation of gene fragments of the library may be achieved by diluting the library to a degree which enables sampling of aliquots containing a gene fragment, preferably an average of one gene fragment per sample and then transferring the samples to separate containers, e.g. microtiter wells. The amplification of the separated gene fragments may be achieved by conventional PCR techniques as well as the in vitro coupled transcription/translation of the amplified gene fragments (see Ohuchi et al. (1998), supra, page 4340 or Ellman et al. (1991), supra, which is hereby incorporated by reference.

In the case of a cellular expression system as a specific embodiment of the invention the screening procedure preferably comprises:

a) pre-propagating and dilution of cells comprising the nucleic acid sequence, b) separating the cells into separate containers, c) propagating separated cells to increase the number of clones of each cell in each separate container, d) contacting the cells in each separate container with a cellulose film of the invention, e) incubating the biological compound with the cellulose film, f) detecting an interaction between the cellulose film and the biological compound and g) recovering gene fragments in containers in which an interaction has occurred Steps a–g may suitably be achieved by use of commercially available standard equipment such as pipettes or automated pipette equipment, flasks, microtiter plates, shakers, thermostated incubators etc.

Pre-propagation and dilution of the cells may in one embodiment of the invention be designed to obtain a concentration of cells per volume suitable for sampling aliquots containing an optimal number of cells to be separated. A suitable average number cells per aliquot may be 0,3-10, preferably 0,3-5, e.g. 0, 3-1.

Pre-propagation of the cells in a preferably aqueous medium preferably provides a 2–5 times increase in the number of cells clones. Suitable incubation temperatures may be within the range of 10–60° C., preferable 30–50° C., e.g. 37° C., while pH may be kept between 4–10, preferably 6–8. The incubation period should be adjusted, preferably 15–60 minutes, e.g. 40 minutes, so as to meet the requirements of the desired transformant and clone concentration.

In the case of the expression system being a culture of host cells wherein transformants comprises a gene library derived from a nucleic acid source, pre-propagation may also be performed to secure expression of an antibiotic marker which may be comprised in the inserted plasmid of transformed host cells enabling resistance to an antibiotic in the medium. Pre-propagation of the host culture may accordingly be achieved by incubation at conditions favorable for expression of the chosen type of antibiotic marker as well as securing viability of the transformant.

Dilution may be performed by addition of a medium, to ensure that all cells and clones thereof resides in the diluted solution.

The cells may be separated by transferring aliquots of the planned specific volume to separate containers, e.g. wells in commercial microtiter plates.

The separated cells are propagated to increase the number of clones in each container, preferably to a range between $10^7$–$10^8$ clones/ml. If microtiter plates are used these plates may be denoted "master plates". For screening a bacterial gene library 50–100 master plates with each 96 wells may typically be employed. One advantage of having a master plate is the possibility of keeping viable samples of the cells to be screened, so that even if the subsequent screening conditions results in death of the screened cells, it is possible to track back a screening result to a viable sample of a screened cell.

In a further preferred embodiment suitable incubation temperatures may be in the range of 10–60° C., preferable 30–50° C., e.g. 37° C., while the pH may be kept between 4–10, preferably 6–8. The incubation medium should meet the nutritional requirements of the cells and clones to ensure sufficient growth.

Also in the case of the expression system being a culture of host cells wherein transformants comprises a gene library derived from a nucleic acid source and an antibiotic marker a medium may suitable be chosen enabling killing or suppressing non-transformed host cells.

Incubation times should be adjusted so as to ensure growth yielding a sufficient number of cells/clones suitable for sampling aliquots containing a suitable number of clones for screening leaving a number of viable clones in the master plate. A preferred propagation period may be 40–90 hours, e.g. 48 hours, depending on the type of microbial host cell and the propagation conditions.

In the case of the expression system being a culture of host cells comprising a gene library in which an antibiotic marker is comprised in transformed host cells the pre-propagation, dilution and/or propagation, in a preferred embodiment of the invention, are performed in a medium capable of selectively killing or suppressing growth of non-transformed host cells. This may preferably be achieved by adding e.g. an antibiotic to the culture medium towards which the transformants or clones thereof are resistant, in an amount effective on non-transformed host cells.

Aliquots of the cells are transferred, e.g. by pipette, to a microtiter plate containing the cellulose film of the invention. The contact between the biological compound and the cellulose film occur via the extracellular medium. In case the biological compound is confined within the interior of the cell, the cell may be lysed or its integrity otherwise disrupted in order to release the biological compound to the medium.

The incubation may be performed at conditions, which favor the reaction between the biological compound and cellulose film. In a preferred embodiment the reaction between the fluorescent substance(s) and the biological compound is optimized with respect to pH and temperature. The incubation may also be performed at extreme conditions (such as very low temperatures (e.g. below 30° C. or below 20° C.) or high temperatures (e.g. above 60° C. or above 70° C.), low pH (e.g. below 5 or below 4) or high pH (e.g. above 9 or above 10), low or high ionic strength, presence of hostile chemicals such as detergents) causing death of the cells, depending on which biological compound is to be detected. If for instance the biological compound to be found is a thermostabile compound the incubation may be performed at high temperatures, conditions providing that only biological compounds, which remain active at high temperatures will react with a cellulose film of the invention.

Nucleic acid sequences in a cellular nucleic acid source or a gene library derived from a nucleic acid source and expressed either in an in vitro expression system or by transformation into a host cell expression system may thus be screened for nucleic acid sequences encoding for biological compounds which reacts with the cellulose film of the invention.

Also the invention relates to nucleic acid sequences encoding a biological compound found by employing the screening method of the invention and to a method for producing a biological compound comprising the steps of a) Identifying in a population of cells or in vitro expression systems, cells or systems which expresses a biological compound by contacting cells of the population with a cellulose film of the invention, b) selecting cells or systems producing the biological compound c) identifying a nucleic acid sequence encoding the biological compound d) Cultivating a cell comprising a nucleic acid sequence encoding the biological compound so as to produce the biological compound and e) recovering the biological compound.

The invention is illustrated by the following examples, which is not in any way intended to be limiting to the scope of the invention.

EXAMPLES

Example 1

Bacterial cellulose microfibrils in an impure form was obtained from the Japanese food stuff "nata de coco" (Fujico Company—Kobe Japan). The cellulose in 350 g of this product were purified by suspension of the product in about 4 L of tap water. This water was replaced by fresh water twice a day for 4 days. Then, 1% NaOH (w/v) was used instead of water and the product was re-suspended in the alkali solution twice a days for 4 days. Neutralisation was achieved by rinsing the purified cellulose with distilled water until the pH at the surface of the product was neutral. The cellulose was microfibrillated and a suspension of individual bacterial cellulose microfibrils was obtained by homogenisation of the purified cellulose microfibrils in a Waring blender for 30 min. The cellulose microfibrils were further purified by dialysing this suspension through a pore membrane against distilled water and the isolated and purified cellulose microfibrils were stored in suspension at 4° C. Diluted suspensions of bacterial cellulose were deposited on carbon coated electron microscope grids and the structure of the isolated cellulose microfibrils was recorded by a Phillips CM 200 Cryo transmission electron microscope (T.E.M.). The results showed that the individual bacterial cellulose microfibrils have a ribbon-like morphology. The width of these microfibrils is of about 100 nm and their thickness estimated from the twist of the microfibrils is in average of 5 nm.

Example 2

The preparation method of example 1 required more than a week to obtain the isolated and purified suspensions of bacterial cellulose microfibrils. Accordingly an alternative preparation method was developed which took only two days without modifying the properties of the bacterial cellulose microfibrils. The cellulose in 350 g of "nata de coco" were rinsed extensively with tap water in order to remove the excess impurities such as of sweeteners and flavours. The partially purified cellulose was separated and were then re-suspended and microfibrillated by homogenisation in water using a Waring blender for 10 minutes. This cellulose microfibril suspension was separated and re-suspended twice in 1% NaOH by centrifugation and kept in the alkali solution under stirring overnight at room temperature. The purified suspension of cellulose microfibrils was neutralised by at least three centrifugations and re-dispersions of the specimen in water. The resulting purified and isolated cellulose microfibrils was treated at 70° C. for 1–2 hours by a bleaching solution consisting of 1 volume part of 1.7% aqueous $NaClO_2$ and 1 volume part of acetate buffer (pH 4.9) completed with 3 volume parts of distilled water. Finally, the bacterial cellulose microfibrils were washed from the bleaching solution by several centrifugations with distilled water. The purified and isolated cellulose microfibrils was homogenised in a distilled water suspension with a Waring blender for 20 min and stored at 4° C.

Example 3

The bacterial MFC having Cellulose I structure obtained as described in example 1 and 2, was converted into Cellulose $III_I$ according to the procedure in Chanzy et al.; *Structural changes of cellulose crystals during the reversible transformation cellulose I to cellulose III; Valonia.* Holzforschung; 40; suppl. 25–30. Microfibrils of bacterial cellulose obtained in example 1 was suspended in pure methanol and was transferred into anhydrous ethylene-diamine after centrifugation. The mixture was kept overnight at room temperature in ethylene-diamine before being re-suspended for few hours in pure methanol. The whole treatment was repeated six time until the complete conversion of cellulose I into the cellulose $III_I$ was observed. The transformation was recorded by X-ray diffractometry and Fourier transform Infra-red spectroscopy. Dried samples of cellulose I microfibrils and cellulose $III_I$ microfibrils were analysed by X-ray with a Warhus flat film camera mounted on Philips PW1720 X-ray generator emitted Ni filtered CuKa radiation operated at 30 kV and 20 mA. When the conversion of native cellulose into cellulose IIIwas not completed intermediate patterns were observed.

For Fourier Transform-Infrared (FT-IR) spectroscopy, drops of cellulose suspensions were dried in a polyethylene cap at 50° C. The films were carefully collected and mounted on the specimen holder before being analysed with a Fourier transform Infra-red Perkin Elmer 1720X spectrometer. The spectra were recorded in the transmission mode with a resolution of 4 $cm^{-1}$ in the range of 4600 to 400 $cm^{-1}$. The conversion of native cellulose into cellulose $III_I$ leads to remarkable modifications of the spectra. The most noticeable transformations are extinction of characteristic peaks of cellulose I at 710 $cm^{-1}$ and 750 $cm^{-1}$ and the appearance of an intense sharp peak at 3480 $cm^{-1}$ characteristic of cellulose $III_I$.

Example 4

Cotton bolls grown in a green house at the Texas Tech University (Lubbock) in 1989 and kept at 4° C. in water with sodium azide were used as starting material. The seeds coated with cellulose fibres were removed from the bolls under water. Still under water, cellulose was separated from the seeds with tweezers and were cut into small fragments with a pair of scissors. The long cellulose fibres were shortened and homogenised with a Waring blender until the large cellulose aggregates had disappeared. Then, the cellulose specimen was microfibrillated in water twice in 1 hour with an APV Gaulin homogeniser. The MFC was re-suspended in 1 N NaOH overnight under stirring. The purification of cellulose microfibrils was followed by a treatment with a bleaching solution as in example 2 for one hour at 70° C. After an extensive washing of the cellulose microfibrils with distilled water by centrifugation, the isolated cotton microfibrils in suspension was stored at 4° C. As in example 1 the structure of the cellulose microfibrils were examined by transmission electron microscopy, which showed that the original cotton fibres were disrupted into microfibrils and microfibril bundles. The mechanical treatments applied to the cotton fibres had induced the delamination of the cellulose into flat bundles 100–500 nm long. Such bundles are composed of the tight association of microfibrils, 5–10 nm in width, that have been partly individualised during the treatment. Individual microfibrils can be seen in the background of the image but more frequently at the surface of the bundles to which they remain associated.

Example 5

The native bacterial cellulose I microfibrils of example 1 and those converted into cellulose $III_I$ from example 3 tested as substrates for cellulases. Test enzymes were *Humicola insolens* complex enzymes, which is a complex of enzymes recoverable from the supernatant when fermenting the fungus *Humicola insolens*; and the endoglucanases V and VI described in Schou C. et al.; *Stereochemistry, specificity and kinetics of the hydrolysis of reduced celludextrins by nine cellulases*; Eur. J. Biochem.; 1993; 217; pp.947–953; and Schulein et al.; "*Humicola insolens, alkaline cellulases*"; in "*Trichoderma reesei cellulases and other hydrolases*"; (eds. Suominen P. et Reinikainen T.); Foundation for Biotechnical and Industrial Fermentation Research; Helsinki; vol. 8; pp 109–116. The procedure was conducted as follows: 75 $\mu$l of enzymes solution (1 mg/ml) was mixed with aliquots of 600 $\mu$l of cellulose (100 $\mu$0g/100 $\mu$l) microfibrils suspended in 50 mM phosphate buffer at pH 6.5. The digestion was achieved at 37° C. without agitation.

The degradation kinetics of cellulose microfibrils were followed by measuring the amount of reducing sugars in the supernatant after centrifugation of the degradation mixture according to the ferricyanide method adapted from the Kidby and Davidson (1973), supra. 100 µl of the assays supernatant were treated in boiling water for 7 min. by 1 ml of the ferricyanide solution that consisted of the mixture of 300 mg of potassium hexacyanoferrate III, 28 g of hydrated sodium carbonate ($NaCO_3$, $H_2O$) and 1 ml of 5M NaOH completed to 1 L with distilled water. The absorbency of the solutions was measured at 420 nm, the concentration of reducing sugars was calculated using standard curve obtained using glucose solutions of known concentration.

Figure 2:
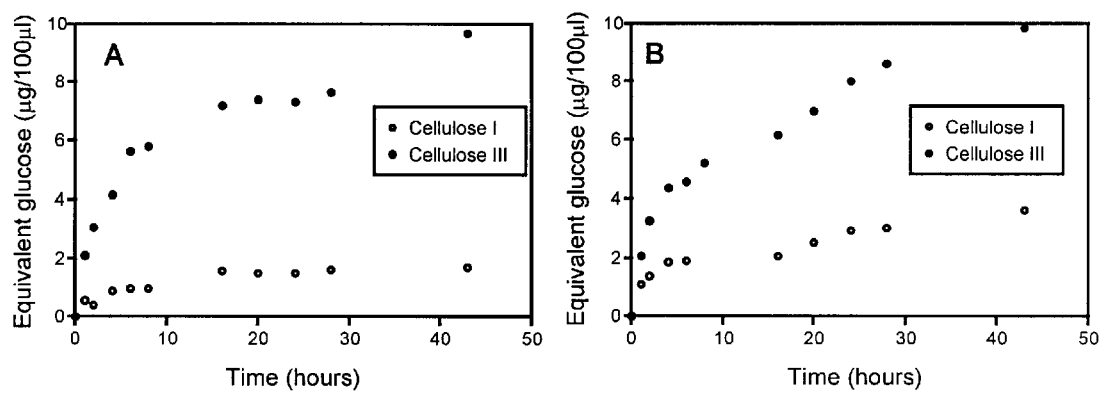
FIG. 2 shows degradation of bacterial Cellulose I and Cellulose III$_I$ by EG V (A) and EG VI (B)

The results are shown in FIG. 1 in which the two curves depict the digestion kinetics of cellulose I and $III_f$ bacterial microfibrils by the *H. insolens* complex. It appears in this illustration that the amount of solubilised reducing sugars produced at extended time is very similar for both substrates. In contrast, the reactivity of the cellulose substrates was markedly different when they were incubated with endoglucanases V or VI as shown in FIGS. 2A and B. Indeed, in FIG. 2, it is observed that the extent of degradation was multiplied by a factor of about 9 and 5 for EG V and EG VI respectively when going from cellulose I to cellulose $III_f$.

Example 6

The fluorescent dye 5-5([4,6-dichlorotriazin-2-YL] amino) fluorescein (DTAF) was attached or grafted on MFC I in a single step procedure. The triazino reactive group of DTAF was known to be quite reactive on the hydroxyl groups of polysaccharides. Consequently, the DTAF molecule was a good candidate for preparing fluorescent cellulose.

One-set MFC grafted with DTAF was prepared by mixing 10 to 70 mg of DTAF (Sigma) with 10 ml of native bacterial cellulose (10 mg/ml) in suspension in 0.1 M NaOH. These mixtures were kept at room temperature for 24 hours under stirring. Then, the cellulose specimens were washed free of unreacted DTAF by at least six centrifugations with distilled water. A second set of derivatised cellulose was prepared as the first set, but the amount of DTAF was in the range of 70 to 115 mg and the concentration in 0.2 M NaOH.

Preliminary experiments revealed that is was not possible to estimate easily and quickly the extent of cellulose labelling by spectroscopic method. Consequently, we incubated labelled cellulose microfibrils with cellulases (*H. insolens* complex, endoglucanases EGV or EGVI) assuming that the release of the fluorescent probe in the supernatant of centrifuged assays should increase with the amount of DTAF grafted onto the surface of cellulose.

Figure 3:
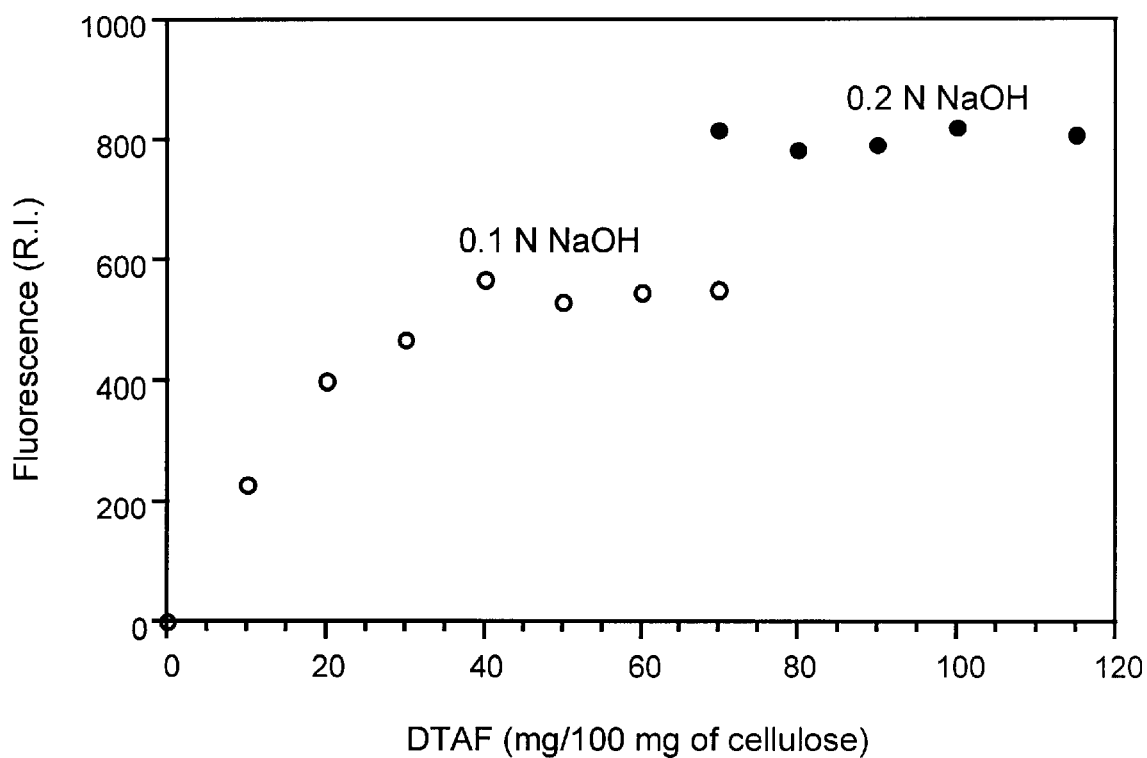
FIG. 3 shows release of DTAF by digestion by H. insolens complex of labelled bacterial cellulose I as a function of grafting conditions.

Tests were performed by adding 20 µl of *H. insolens* complex (1 mg/ml) to 600 µl of labelled cellulose (100 µg/100 µl) in 50 mM phosphate buffer. The mixtures were incubated for 4 hours at 37° C. without agitation. In parallel, control experiments were conducted using water instead of enzyme in order to visualised the non specific release of the fluorescent probe. Supernatants of the corresponding assays collected after centrifugation were diluted 4 times with distilled water. The fluorescence of 200 µl of each specimens was recorded using distilled water as control. For each assay, the relative intensity (R.I.) of fluorescence release during the enzymatic digestion was deduced by subtracting the fluorescence of the test containing the enzyme from its corresponding control test. In FIG. 3, it is observed that when the chemical reaction was conducted in 0.1 M NaOH, the release of the fluorescent probe increases until the amount of DTAF used was of about 40 mg/100mg of MFC. When higher concentration of DTAF was reacted with MFC, the intensity of fluorescence remained constant, suggesting that the level of grafting did not increase. For the set of grafting experiments performed in 0.2 M NaOH, the amount of DTAF solubilised after the enzymatic treatment is higher than when the labelling was done in 0.1 N NaOH. Nevertheless, the release of the probe was constant and did not increase with the amount of DTAF. Consequently, a single-step grafting experiments allowed to reach only a limited range of derivatisation of the MFC.

Example 7

DTAF was attached or grafted on MFC I in a multi-step procedure. A first series of cellulose labelling assays was conducted by mixing 30 mg of DTAF with 10 ml of native cellulose suspension (10 mg/ml) in 0.1M NaOH. The mixture was stirred for 24 hours at room temperature. Then, the specimens were washed extensively by centrifugation with distilled water. The above procedure was repeated several times (steps) and cellulose suspensions were stored at 4° C. A second series of assays was performed according to the same conditions excepted that DTAF was added by steps of 60 mg and the alkali reaction medium was of 0.2M NaOH.

Tests of the enzymatic degradation of the labelled MFC was achieved as for the single-step experiments: samples of 600 µl of grafted MFC suspension (100 µg/100 µl) in 50 mM phosphate buffer at pH 6.5 were mixed with 20 µl of the *H. insolens* complex (1 mg/ml), or 20 µl of EG VI (1 mg/ml) or 20 ml water as standard. Assays were conducted for 4 hours at 37° C. without agitation. Supernatants of the respective centrifuged specimens were analysed by the ferricyanide method to measure the concentration of soluble reducing sugars and by spectrofluorometry to estimate the range of release of the fluorescent probes.

Figure 4:
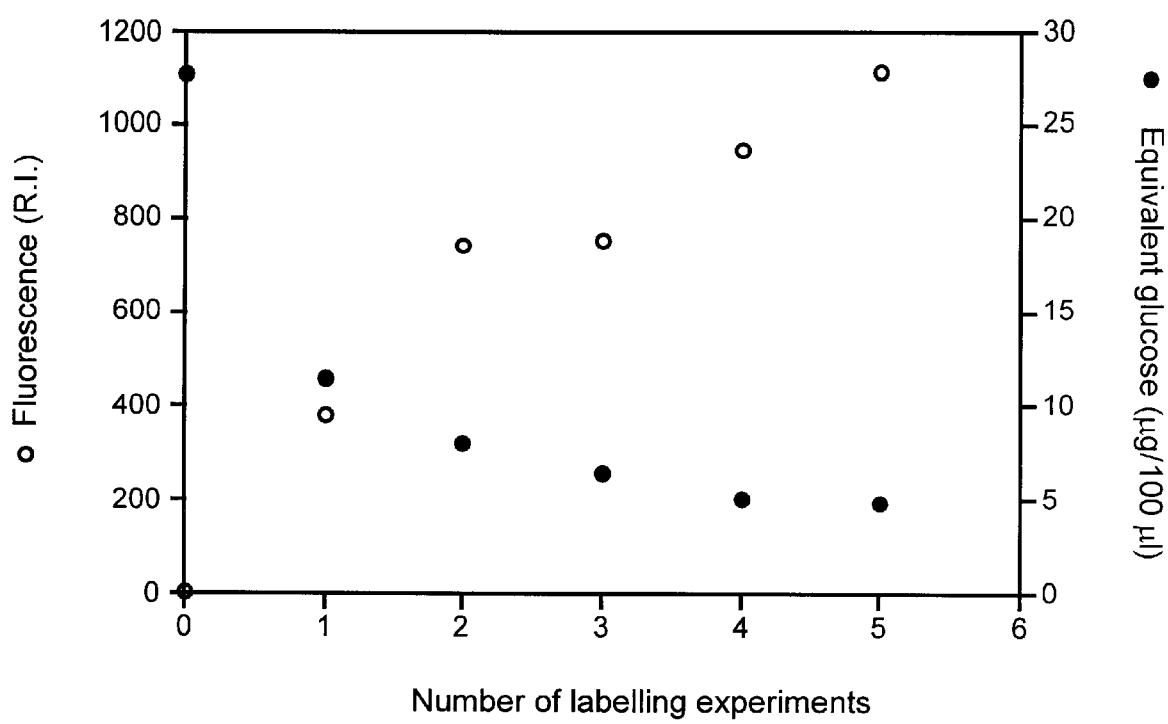
FIG. 4 shows release of DTAF by digestion by H. insolens complex of labelled bacterial cellulose I as a function of grafting steps using 30 mg of DTAF in 0.2 N NaOH.
Figure 5:
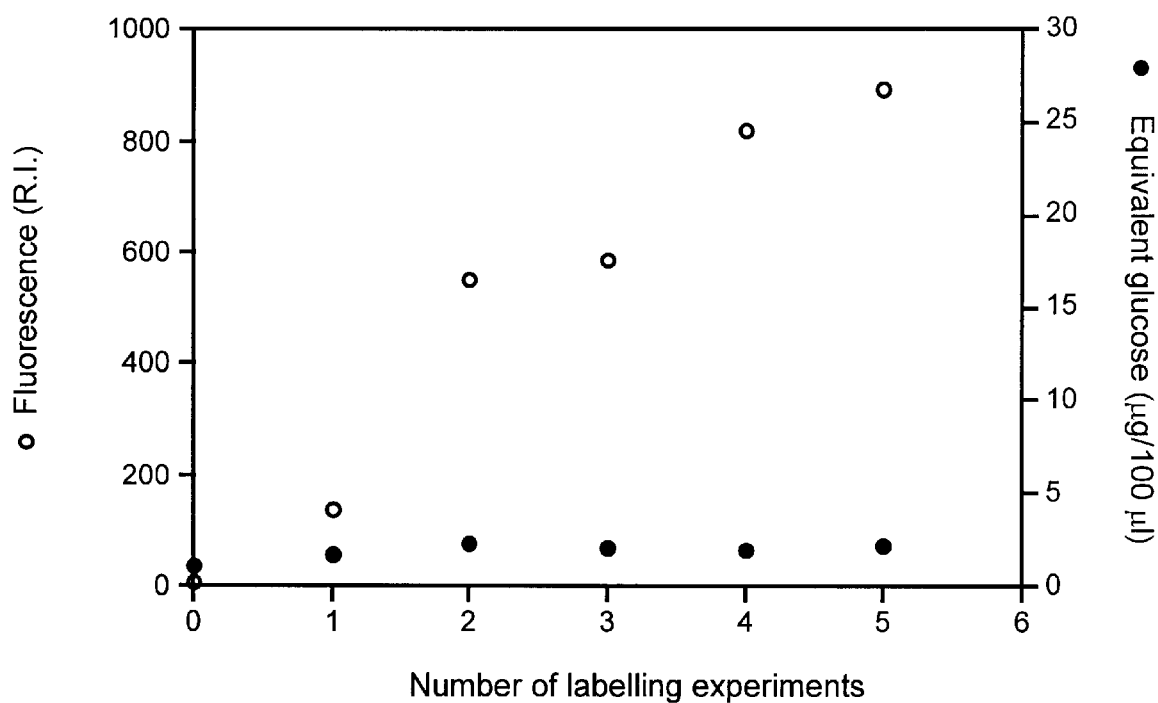
FIG. 5 shows release of DTAF by digestion by EG VI of labelled bacterial cellulose I as a function of grafting steps using 30 mg of DTAF in 0.2 N NaOH.

The results on incubating the first series of labelled cellulose with *H. insolens* complex and EG VI, shown in FIGS. 4 and 5 respectively, leads to a strong release of the fluorescent probes which was diluted 8 time to scale down the intensity in the range of the spectrofluorometer sensibility. In FIG. 4, the increase of fluorescence with the number steps of labelling experiments indicates that the number of DTAF molecule linked to the surface of the cellulose microfibrils increased as well. Also, the decrease of the soluble reducing sugars produced during enzymatic attack when the grafting increase can be easily interpreted as an inhibition of the enzyme by the grafted molecules that cover the surface of cellulose.

The degradation of the labelled cellulose by EG VI is shown in FIG. 5. As for *H. insolens* complex, the fluorescence did increase with the number of labelling experiments. However, inhibition of the enzyme because of the labelling does not seem to occur, the concentration of the reducing sugars solubilised being quite constant. But, it should be noticed that the amount of soluble reducing sugar is quite low and that the ferricyanide method detection may not allow to evidence easily very fine variation in their concentration.

Figure 6:
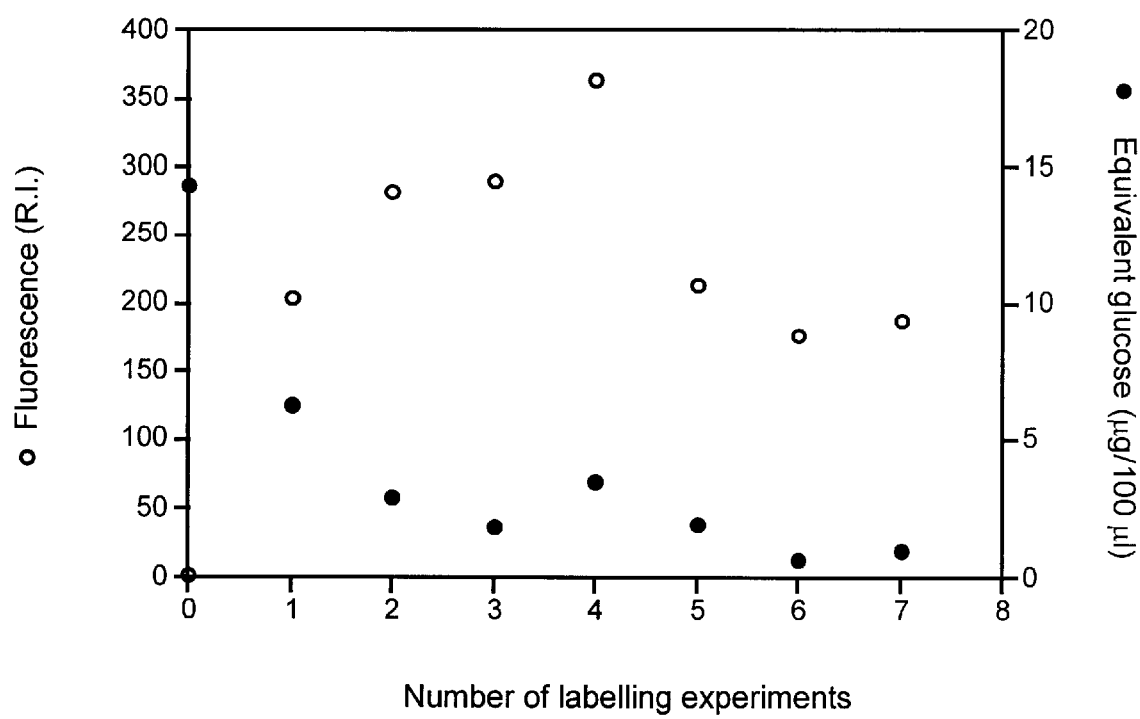
FIG. 6 shows release of DTAF by digestion by H. insolens complex of labelled bacterial cellulose I as a function of grafting steps using 60 mg of DTAF in 0.2 N NaOH.
Figure 7:
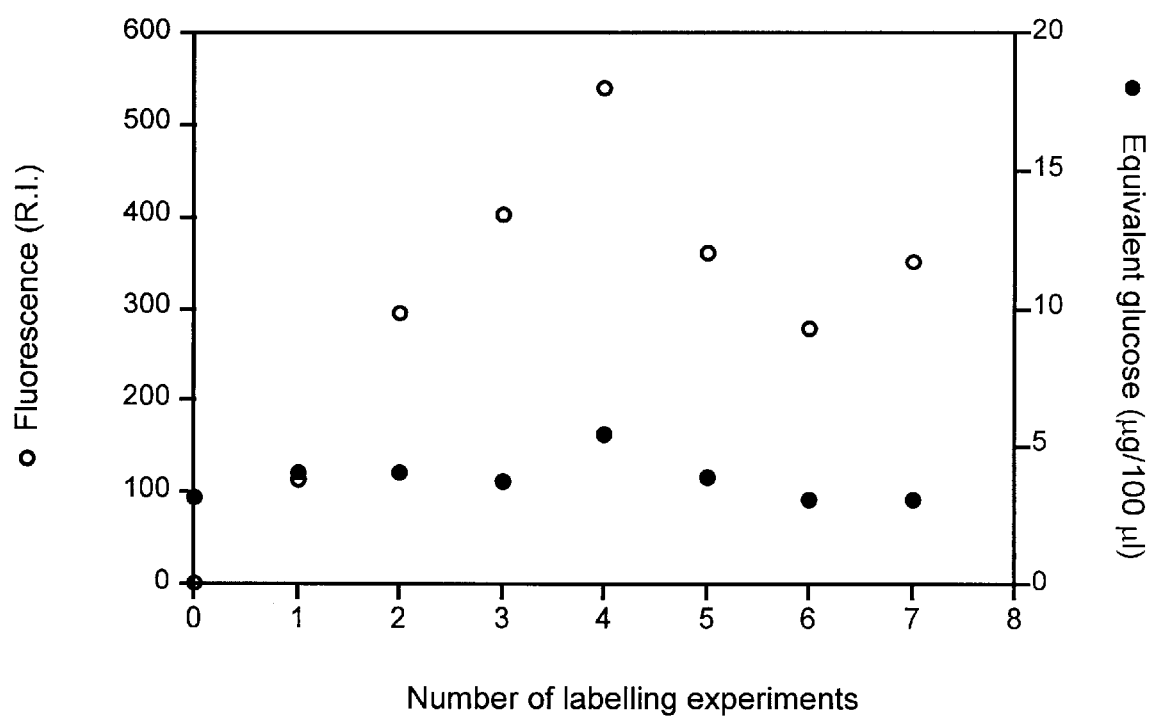
FIG. 7 shows release of DTAF by digestion by EG VI of labelled bacterial cellulose I as a function of grafting steps using 60 mg of DTAF in 0.2 N NaOH.

FIGS. 6 and 7 shows the results of degradation experiments on MFC that was grafted by a number of steps with 60 mg of DTAF in 0.2 N NaOH. In both cases, the action of the enzymes—*H. insolens* complex or EG VI—leads to an increase of the fluorescence until a maximum was observed for MFC grafted four times. For MFC grafted more than four times a decrease of the fluorescence is detected. In the case of *H. insolens* complex (FIG. 6), the variation of fluorescence is clearly associated with a regular decrease of the concentration of soluble reducing sugars that is consistent with an inhibition of the enzymes by the linked DTAF molecules onto cellulose microfibrils. This suggest that for the four first steps of times of labelling, the increase in amount of fluorescent sugars solubilised is more important than the decrease of total amount of reducing sugars. When the inhibition of the enzyme becomes stronger, the amount of grafted sugars released is markedly reduced leading to a decrease of the fluorescence. The same interpretations of the results obtained with EG VI presented in FIG. 7 could be done except that the inhibition of the enzyme could not be evidenced clearly with the ferricyanide method.

Example 8

Figure 8:
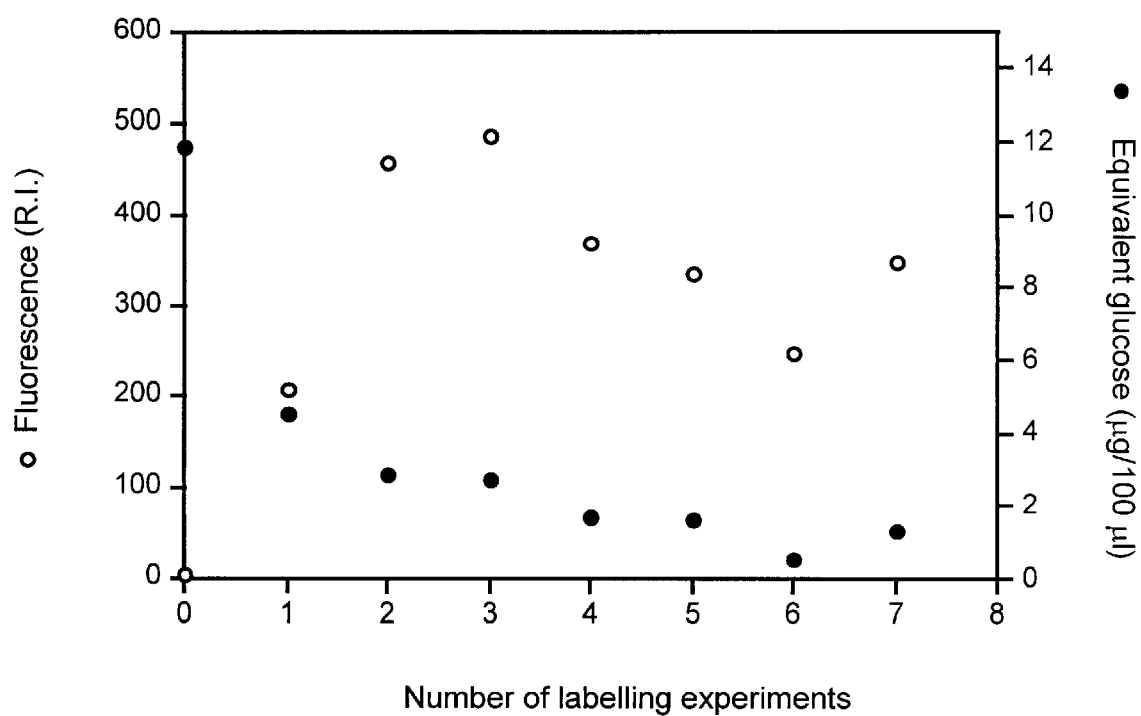
FIG. 8 shows release of DTAF by digestion by H. insolens complex of labelled bacterial cellulose III$_I$ as a function of grafting steps using 60 mg of DTAF in 0.2 N NaOH.
Figure 9:
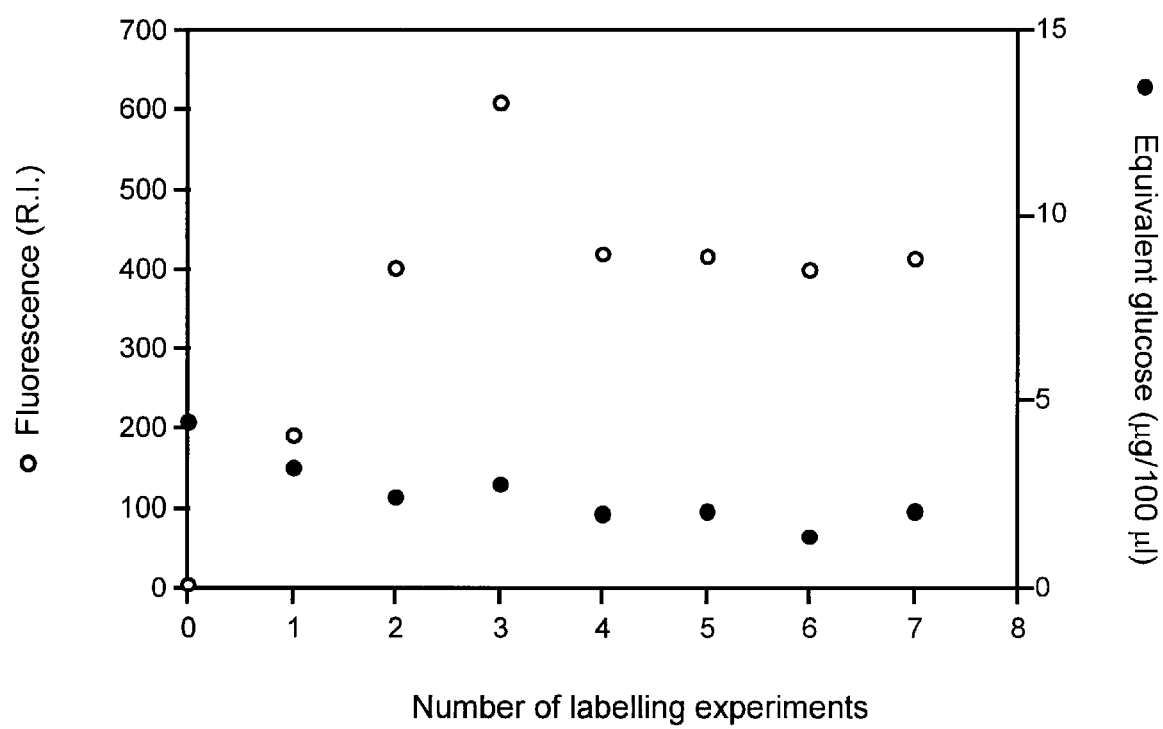
FIG. 9 shows release of DTAF by digestion by EG VI of labelled bacterial cellulose III$_I$ as a function of grafting steps using 60 mg of DTAF in 0.2 N NaOH.

DTAF was attached or grafted on MFC $III_I$ in a multi-step procedure. The grafting of DTAF on MFC $III_I$ was achieved according to the same procedure described in example 7 using 60 mg of DTAF in 0.2 N NaOH. As for the MFC I, the grafted MFC $III_I$ was incubated with cellulases and the results of the degradations using 16 times diluted samples are shown in FIGS. 8 (*H. insolens*) and 9 (EG VI). The variation of fluorescence follows the same behaviour as that of the grafted MFC I. However, the maximum release of the probe was obtained when the cellulose $III_I$ was reacted three times with 60 mg of DTAF (0.2 N NaOH) instead of four times with MFC I. The inhibition of the *H. insolens* complex is also clearly visible by the regular decrease of reducing sugars produced when the level of grafting increase. Also, in the case of EG VI, it is observed in FIG. 9, that the amount of reducing sugar produced decreases with amount of grafted DTAF.

As it was showed in example 5, MFC $III_I$ is more reactive towards endoglucanases than microfibril-lated cellulose I. This was evidenced by an increase of the total amount of reducing sugars solubilised. Also, the labelled MFC $III_I$ is more reactive than the labelled MFC I leading to an increase of the reducing sugars liberated in the incubation medium. Consequently, the ferricyanide method which did not seem sensitive enough according to our procedure with MFC I allowed to reveal the inhibition of EG VI by the grafted cellulose $III_I$.

Example 9

Films of MFC I was prepared. Suspensions of various concentration of MFC in water in the range of 0.3 mg/ml to 2 mg/ml were maintained at room temperature without agitation to allow sedimentation of MFC. After few hours, MFC I of the less concentrated suspensions (0.3 mg/ml–0.7 mg/ml) had sedimented. However, for the more concentrated suspensions (=1 mg/ml), the cellulose did not sediment even after several days. In the case of MFC $III_I$, the sedimentation of cellulose was observed when the concentration of the suspensions was lower than 1.5 mg/ml.

Deposition of MFC on the bottom of 96 well microtiter plate (Nunc-immuno PlateMaxsorp™, Nunc) were achieved by drying at 37° C. various volumes of suspensions of MFC (50, 100 and 200 μl) of various concentration (0.1 mg/ml to 2 mg/ml). It appeared rapidly that the films did not stick onto the surface of the wells when the total amount of dried MFC was more than 150 mg. Also, when the volume of suspensions was superior to 200 ml, the cellulose adhered onto the wall of the well in a non reproducible fashion. It was found that the best films were obtained with 100 μl of suspension having a concentration of about 1 mg/ml or below.

Example 10

Enzymatic degradation of unlabelled films was tested. Films of MFC I were obtained by drying 100 μl of cellulose I suspensions (1 mg/ml) at 37° C. per well of a 96 well microtiter plates. The reproducibility of the films was tested towards their susceptibility to enzymatic degradation: 200 μl of 50 mM phosphate buffer at pH 6.5 followed by 20 μl of *H. insolens* complex (1 mg/ml) were added in each well and kept at 37° C. At various incubation times, 8 samples of 100 μl were collected and the amount of solubilised reducing sugars produced were measured by the ferricyanide method. The average and the standard error were calculated according to the following equations where n is the number of samples and x the amount of reducing sugars.

$$\text{Average} = \overline{X} = \frac{\sum_{1 \to n} x_n}{n}$$

$$\text{Standard error} = \sigma = \sqrt{\frac{\sum_{1 \to n} x^2 - \left(\sum_{1 \to n} x_n\right)^2}{n^2}}$$

The following table showes the average values and the corresponding standard errors for 5 different times of degradation of the films by *H. insolens* complex.

| | Cellulose I films Equivalent glucose solubilised (mg/100 ml) | | | Cellulose $III_I$ films Equivalent glucose solubilised (mg/100 ml) | |
| --- | --- | --- | --- | --- | --- |
| Time (h) | Average | Standard error | Time (h) | Average | Standard error |
| 0 | 0 | 0.46 | 0 | 0 | 0.26 |
| 1 | 1.54 | 0.57 | 1 | 1.47 | 0.43 |
| 2 | 3.07 | 1.53 | 2 | 2.79 | 1.14 |
| 4 | 6.89 | 1.86 | 4 | 7.77 | 1.25 |
| 6 | 13.29 | 1.88 | 6 | 13.07 | 1.44 |

The kinetics of degradation of the films of cellulose I and cellulose $III_I$ are very similar. This behaviour is in agreement with the kinetics experiments performed in the case of suspensions. The reproducibility of the films deposition have been tested by an indirect method that include several experimental steps such as dilution and chemistry. Consequently, the resulting calculated standard errors comprised the errors on the films formation and others experimental errors as well.

Example 11

Enzymatic degradation of labelled films was tested. Films of MFC were obtained by drying 100 μl of cellulose suspensions (1 mg/ml) at 37° C. per well of a 96 well microtiter plates. The tested MFC was that which allowed the maximum release of fluorescence after incubation with cellulases in suspension. The MFC used for making the film was accordingly grafted by 4 repeated labelling steps with 60 mg DTAF in the case of cellulose I and 3 grafting steps in the case of cellulose $III_I$.

The reactivity of the films were assayed towards EG V and EG VI activities. 10 μl of the enzymes (0.1 mg/ml) were deposited in the wells containing 200 μl of 50 mM phosphate buffer pH 6.5. The microtiter plates were kept at 37° C. At various times of degradation, 8 samples were collected and diluted 8 times and 200 μl of these dilutions were analysed by spectrofluorometry. The average and the standard error values calculated from the fluorometry data recorded on the labelled MFC I and cellulose $III_I$ shows from the following tables:

| Cellulose I Time (h) | No enzyme Fluorescence (R.I.) | | EG V Fluorescence (R.I.) | |
|---|---|---|---|---|
| | Average | Standard error | Average | Standard error |
| 0 | 148.07 | 15.52 | 145.93 | 28.09 |
| 1 | 175.02 | 17.12 | 260.2 | 43.15 |
| 2 | 214.42 | 20.98 | 361.36 | 65.93 |
| 3 | 221.43 | 29.65 | 424.11 | 79.26 |
| 4 | 230.70 | 31.68 | 405.70 | 78.96 |
| 5 | 225.84 | 32.11 | 416.98 | 91.41 |

| Cellulose III Time (h) | No enzyme Fluorescence (R.I.) | | EG V Fluorescence (R.I.) | | EG VI Fluorescence (R.I.) | |
|---|---|---|---|---|---|---|
| | Average | Standard error | Average | Standard error | Average | Standard error |
| 1 | 62.03 | 8.50 | 52.93 | 16.33 | 65.25 | 7.94 |
| 2 | 81.14 | 10.70 | 325.52 | 67.08 | 237.60 | 34.88 |
| 3 | 86.45 | 14.047 | 539.80 | 115.60 | 385.31 | 48.28 |
| 4 | 85.34 | 14.86 | 517.90 | 136.20 | 441.46 | 70.47 |
| 5 | 88.31 | 19.13 | 544.62 | 137.12 | 481.05 | 84.57 |
| 6 | 87.45 | 18.15 | 567.90 | 150.10 | 427.07 | 137.99 |

For both the cellulose systems and whatever the endoglucanase tested, the fluorescence release seems to occur according the same pattern. The fluorescence increase linearly until a maximum which was reached after 3 to 4 hours incubation with enzyme. When no enzyme was present in the reaction medium, the maximum intensity of the non specific fluorescence is observed more quickly, usually in less than 2 hours.

Concerning the reproducibility of the kinetics followed by the fluorescence release, it is observed that this system allow within the experimental errors to evidence minute amount of endoglucanes in less than 1 hour. It is important to notice, that the standard errors recorded is the sum of experimental errors. Some of these have occurred certainly after the numerous dilutions necessary to scale down the strong fluorescence intensity with the spectrofluorometer sensitivity.

The labelled cellulose substrates do not have the same behaviours. Indeed, in the case of EG V, it is observed that the use of cellulose $III_I$ instead of cellulose I allows a gain of fluorescence release of a factor 2.5.

Example 12

Figure 10:
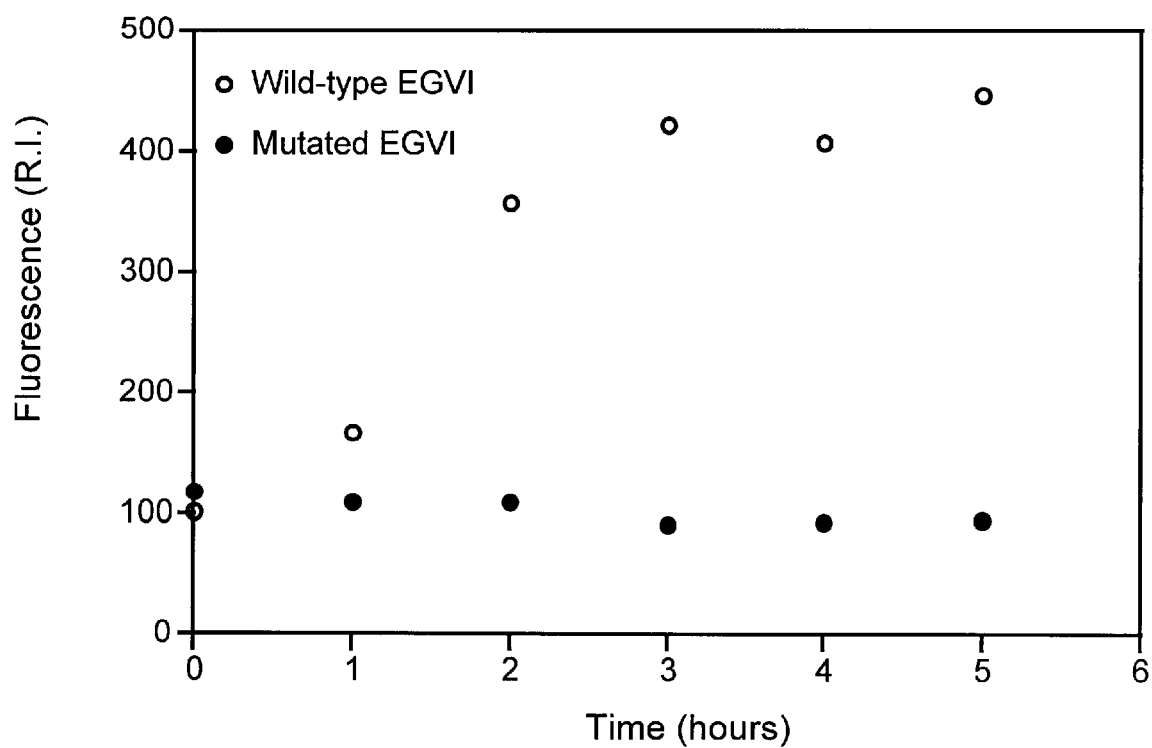
FIG. 10 shows release of DTAF by digestion by active EG VI and inactive mutant EG VI of labelled bacterial cellulose III$_I$ as a function of incubation time.

Experiments using yeast extracts were performed on films of labelled MFC. The results presented in FIG. 10 were obtained by incubating films of cellulose $III_I$ with 200 $\mu$l of 50 mM phosphate buffer pH 6.5 to which was added 50 $\mu$l of yeast extract. Despite strong quenching, it was possible to follow the increase of fluorescence at various time of degradation when the yeast extract containing active EG VI. The solubilisation of the fluorescent probes increased until a maximum was reached in 3 hours. The difference in fluorescence intensities between the yeast extract containing the active EG VI and one having a mutated inactive EG VI, suggests that the EG VI activity could be reasonably detected in less than 2 hours.

Example 13

DTAF was attached or grafted on MFC in a multi-step procedure as described in example 7: 60 mg of DTAF was added to 10 ml of cellulose suspension (10 mg/ml) in 0.2M NaOH. The mixture was stirred for 24 hours at room temperature. Then, the specimens were washed extensively by centrifugation with distilled water. The labelling was performed several time and the final cellulose suspensions were stored at 4° C.

Example 14

Figure 11:
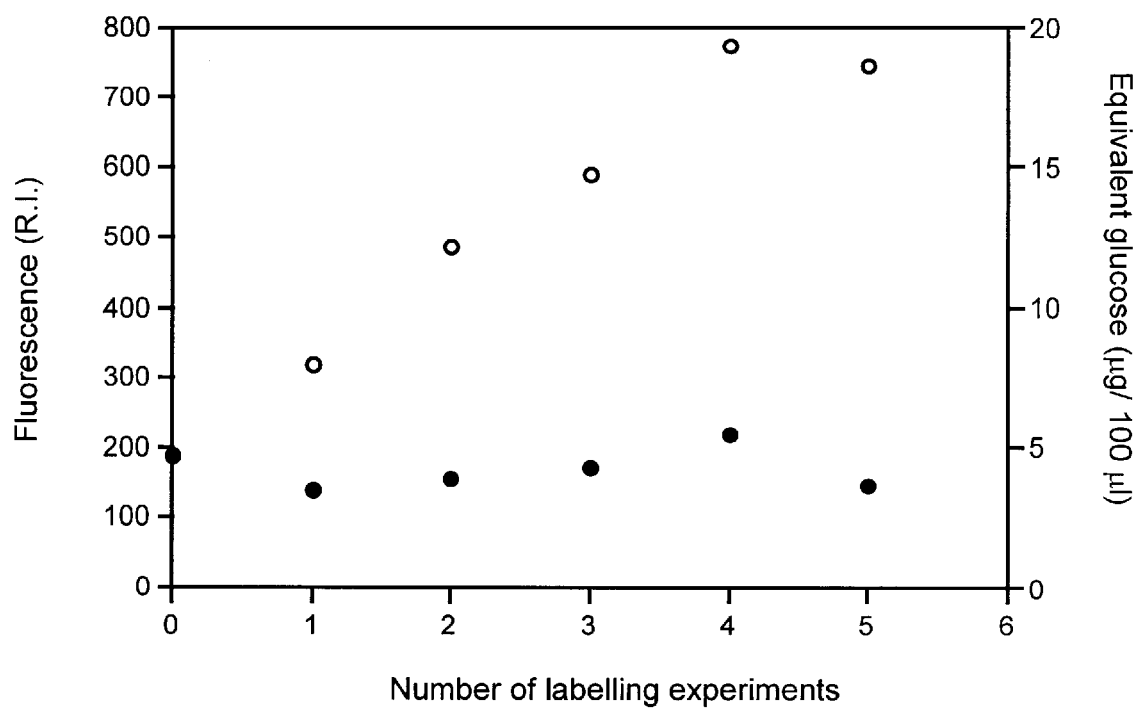
FIG. 11 shows release of DTAF by digestion by EG V of labelled cotton cellulose I as a function of grafting steps using 60 mg of DTAF in 0.2 N NaOH.
Figure 12:
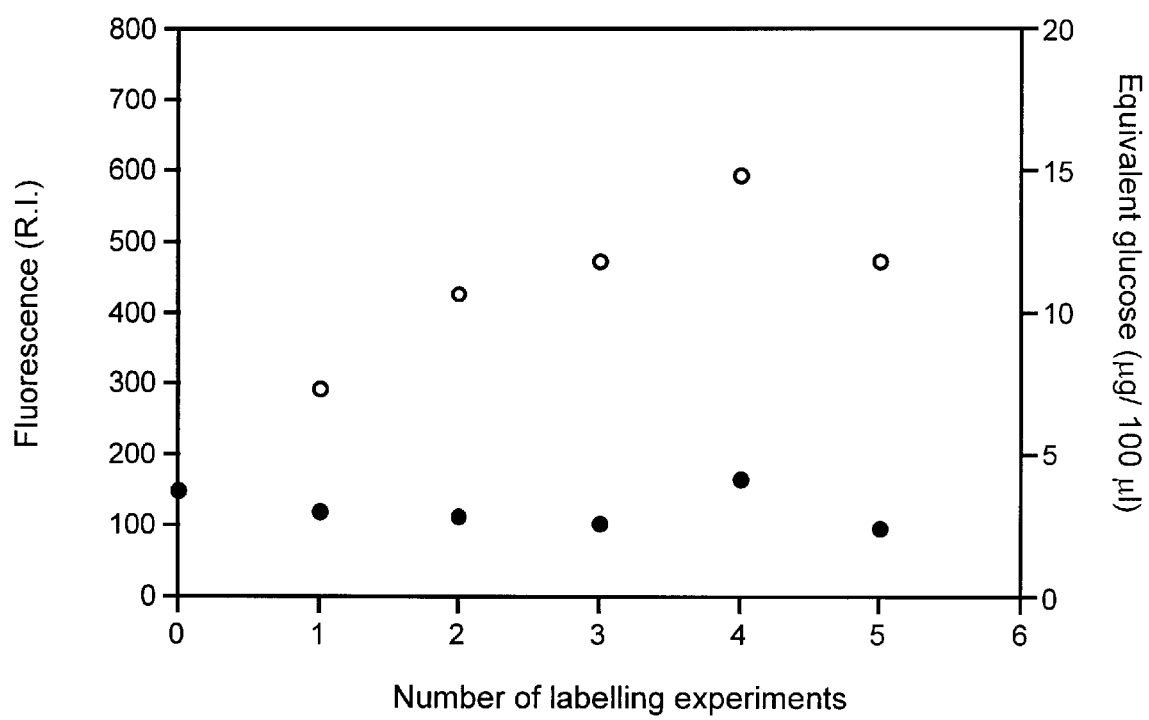
FIG. 12 shows release of DTAF by digestion by EG VI of labelled cotton cellulose I as a function of grafting steps using 60 mg of DTAF in 0.2 N NaOH.

The labelled of microfibrillated cotton cellulose of example 13 was tested towards EG V and EG VI. 600 $\mu$l of grafted cellulose suspension (100 $\mu$g/100 $\mu$l) in 50 mM phosphate buffer at pH 6.5 were mixed with 20 $\mu$l of enzyme (1 mg/ml) or 20 $\mu$l of water as control or standard. The hydrolysis was conducted for 4 hours at 37° C. without agitation. Supernatants of the respective centrifuged test solutions were analysed by the ferricyanide method and by spectrofluorometry. FIGS. 11 and 12 shows the release of fluorescence in samples diluted 16 times as a function of the number of labelling steps when the labelled of microfibrillated cotton cellulose were incubated with EG V and EG VI respectively. In both cases, the variation of fluorescence follows the same behaviours as that observed for bacterial cellulose. Indeed, the amount of fluorescent probes increase with the number of labelling steps until a maximum reached for the fourth grafting steps. Beyond that, the detected fluorescence intensity decreased for the most grafted cellulose. The number of steps that are necessary to obtain a maximum of fluorescence release in the case of microfibrillated cotton cellulose is identical to what we previously observed with bacterial cellulose I.

Example 15

Films of microfibrillated cotton cellulose was prepared. The cellulose films were obtained according to the same procedure described in example 9: 100 $\mu$l of cellulose suspensions (1 mg/ml) per well of microtiter plates were dried overnight at 37° C.

Example 16

The reactivity of films of unlabelled microfibrillated cotton cellulose were tested towards the H. insolens complex. Each well of the micro-titer plates were filled with 200 $\mu$l of 50 mM phosphate buffer at pH 6.5 followed by the addition of 20 $\mu$l of H. insolens complex (1 mg/ml). The mixtures were kept at 37° C.

At various time of incubation, 8 samples of 100 $\mu$l were collected and the amount of solubilised reducing sugars produced were measured by the ferricyanide method. Averages and standard errors values calculated from the sets of data are shown in the following table:

| Time (hours) | Equivalent glucose solubilised (mg/100 ml) | |
|---|---|---|
| | Average | Standard error |
| 0 | 0 | 0.28 |
| 1 | 2.21 | 0.66 |
| 2 | 5.13 | 1.27 |
| 4 | 9.87 | 1.75 |
| 6 | 17.66 | 1.19 |

The degradation kinetics, the standard error of the overall experiment including films deposition, dilution, and the reducing sugars test was in agreement with a good reproducibility of the film deposition as it was observed previously for the bacterial cellulose I and III$_f$.

Example 17

The reactivity of films towards enzymes was assayed with the labelled microfibrillated cotton cellulose which allowed the maximum release of fluorescence after incubation with enzymes. This labelled cotton cellulose was obtained after 4 repeated labelling steps with 60 mg DTAF in 0.2 M NaOH.

The degradation of the films was performed by adding 10 μl of EG V and EG VI (0.1 mg/ml) to 200 μl of 50 mM phosphate buffer pH 6.5 deposited in the wells of the microtiter plates. The samples were kept at 37° C. At various degradation time, 8 samples were collected and diluted 8 times. 200 μl of these diluted solutions were analysed by spectrofluorometry. The average and the standard error values calculated from the recorded data are shown in the following table:

| Time (hours) | No enzyme Fluorescence (R.I.) | | EG V Fluorescence (R.I.) | | EG VI Fluorescence (R.I.) | |
| --- | --- | --- | --- | --- | --- | --- |
| | average | Standard error | Average | Standard error | Average | Standard error |
| 0 | 206.08 | 15.76 | 197.60 | 24.07 | 232.47 | 29.66 |
| 1 | 245.22 | 17.34 | 325.12 | 52.44 | 328.25 | 56.06 |
| 2 | 287.01 | 25.85 | 454.82 | 87.93 | 457.45 | 73.18 |
| 3 | 289.89 | 30.56 | 549.99 | 95.97 | 526.94 | 53.86 |
| 4 | 277.01 | 22.51 | 547.62 | 117.77 | 539.83 | 52.38 |
| 5 | 271.00 | 33.43 | 573.95 | 121.79 | 567.67 | 66.67 |

The degradation pattern of the labelled cellulose films were very similar to those that were obtained with bacterial cellulose I in term of intensity of the fluorescence and kinetics of solubilisation of the probes. Consequently, as for bacterial cellulose it seems reasonable that the endoglucanase activities could be detected in less than 2 hours with the use of such labelled cellulose films.

Example 18

Haemoglobin was labelled with Fluoresceinisothiocyanate; Isomer I (FITC). 17.500 g bovine hemoglobin (Sigma H-2625) was dissolved in 600 mL 0.25 M sodium-buffer (pH=9.0). 75 mg FITC (Sigma F-1522) dissolved in 250 mL 0.25 M sodium-buffer (pH=9.0) was added drop-wise over 10 minutes under vigorous stirring. The mixture was allowed to react in dark at room temperature for 1 hour. Excess of FITC was removed by ultra filtration on a Filtron Amicon RA2000 against PBS-buffer (containing 80.0 g NaCl (Merck 6404), 2.0 g KCl (Merck 4936), 10.4 g $K_2HPO_4$ (Mecrk 5101), and 3.17 g $KH_2PO_4$ (Merck 4873) in 10.00 L miliQ water; pH=7.2 ).

Example 19

Galactomannan (Locust bean gum) was labelled with Fluorescein-5-thiosemicarbazide. 3.0032 g Galactomannan (Sigma G-0753) dissolved in 250 mL miliQ water was oxidised at room temperature for 48 hours using Galactoseoxidase (Cibrina candolleana 8637/F9700806). The oxidation was followed by light-absobance ($Abs_{410}$), after treating a small sample with a few drops of a PHBAH-reagent (containing 150 mg p-hydroxybenzosyrehydrazid, and 500 mg Potassium-sodium-tartrate in 10.0 mL 2% NaOH-solution) at 95° C. for 5 minutes. The enzyme was inactivated by heating the mixture to 90° C. for 5 min. 75.2 mg fluorescein-5-thiosemicarbazide (Molecular Probes F-121) dissolved in 2 mL DMF was added, and the mixture was allowed to react at room temperature in dark for 48 hours. The labelled polymer was precipitated in 400 mL MeOH and was subsequently washed using EtOH until the supernatant no longer contained probe. The labelled polymer was re-dissolved in water and freeze-dried. Produced amount: 2.112 g.

Example 20

A new batch of Bacterial Cellulose I was prepared: The contents of 3 cans of Nata de Coco containing approximately 900 g wet bacterial cellulose from *Acetobacter Xylium* in cubes was washed in 10 L demineralised water. The cubes were then washed in 3 L 1% NaOH solution. The soda was changed twice every day for 5 days. The cubes were finally washed in 3 L demineralised water. The water was changed twice every day for 5 days. The cubes were homogenised in a warring blender and dialysed against demineralised water (Cut-off 12-14000) for 4 days.

Example 21

Cellulose films containing labelled haemoglobin or labelled galactomannan were prepared: Suspended bacterial cellulose of example 20 (1 mg/ml) was mixed with 500 μg/ml fluorescein labelled haemoglobin or 50 μg/ml fluorescein labelled galactomannan (Locust bean gum galactomannan) and 25 μg/ml Keltrol T xanthan (Kelco, Chicago, USA) prior to being dispersed and microfibrillated using a Polytron PT 3000 (Kinematica, Switzerland) for 3 minutes at 10.000 rpm. 100 μl, 20 μl, and 3 μl of this mixture was added to each well of 96, 384, and 1536 well plates respectively, and dried over night at 37° C. The microtiter plates was 96 well (cat. # 442404) and 384 well (cat. # 464718) plates with Maxisorp™ surface obtainable from NUNC, Denmark and the 1536 well plates were obtained from Greiner labortechnik, Germany, cat. # 782101.

Enzymes were detected using the prepared film of example 21. All enzymatic detections were conducted in 50 mM HEPES pH 8.0 with 1 mM $CaCl_2$. For detections conducted in 96, 384 and 1536 wells microtiter plates 165 μl, 80 μl and 8 μl of the diluted enzyme were added to each well, respectively. The reaction was incubated at 40° C. for 40 minutes at 700 rpm in a Thermostar (BMG, Germany). When 96, 384 and 1536 wells plates were applied samples of 100 μl, 60 μl and 4 μl were transferred, respectively, after the incubation to a new black microtiter and analysed for fluorescence intensity on a Polarstar Galaxy (BMG, Germany) equipped with the appropriate light guides. Black 96, 384 and 1536 wells plates were obtained from Bibby Sterilin, England, cat # 611F96BK; NUNC, Denmark, cat # 264556; and Greiner labortechnik cat # 782076, respectively.

Example 22

Protease activity of two different proteases was detected using the films containing labelled haemoglobin and the detection method of example 21. In the following table the amount of removed labelled haemoglobin in % w/w are shown for 96, 384 and 1536 well plates:

|  | 96 well plate | 384 well plate | 1536 well plate |
| --- | --- | --- | --- |
| Savinase ® | | | |
| 0.25 µg/ml | 42% | 47% | ND |
| 0.5 µg/ml | 50% | 66% | 42% |
| 1.5 µg/ml | 100% | 100% | 100% |
| C-component | | | |
| 0.25 µg/ml | 16% | 21% | ND |
| 0.5 µg/ml | 10% | 12% | ND |
| 1.5 µg/ml | 12% | 14% | ND |

Savinase® is a commercially available protease from Novo Nordisk A/S, while component C is the glutamic acid specific protease described in Kakudo S. et al.; *Purification, Characterization, Cloning and Expression of a Glutamic acid-specific Protease from Bacillus lichiniformis ATCC 14580*; J. Biol. Chem.; 1992; vol. 267; No. 33; pp 23782–23788. ND means not determined.

As shown the removal fluorescent Labelled haemoglobin in the 96, 384 and 1534 well plate format corresponds very well demonstrating that detection of enzymes may be scaled down to very small volumes.

Example 23

Mannanase activity of four different mannanases was detected using the films containing xanthan and labelled galactomannan and the detection method of example 21. In the following table the amount of removed labelled galactomannan in % w/w are shown for 96 well plates relative to BXM 3 (10 µg/ml BXM 3=100%):

|  | 0.2 µg/ml | 10 µg/ml |
| --- | --- | --- |
| BXM 1 | 9% | 36% |
| BXM 3 | 65% | 100% |
| BXM 5 | 40% | 92% |
| BXM 7 | 0% | 21% |

BXM1, BXM5 and BXM7 is described in the international patent application PCT/DK99/00314.

The results shows that using a cellulose film containing labelled galactomannan different mannanases may be ranked and BXM 3 may be selected as showing the best performance.

Example 24

A comparison of detecting the mannanase activity by the method of example 21 and detecting mannanase activity using textile swatches were made: In order to dye textile swatches with fluorescently labelled galactomannan, the textile was submerged into a aqueous solution of 0.225 g/l unlabelled Locust bean gum (Sigma, USA), 0.025 g/l fluorescein labelled Locust bean gum and 0.125 g/l Keltrol T xanthan (Kelco, Chicago, USA). The textile was then put through a roller in order to remove any surplus of dye solution and subsequently air dried over night in the dark. Finally the dyed textile was rinsed twice for 1 hour in 14 l distilled water with 2 g/l detergent and air dried in the dark.

Detection of mannanase activity using textile swatches was done by incubating solutions of mannanase (BXM 3) with the labelled textile swatch for 40 minutes at 40° C., while shaking at 700 rpm. Subsequently, the solution was aspirated applying a plate washer (EL 403H, Bio-Tek Instruments, Vermont, USA) and the fluorescence of the labelled galactomannan remaining in the textile was measured by the use of a Polarstar Galaxy (BMG, Germany).

Detection of Mannanase activity using labelled cellulose film was done using the films containing xanthan and labelled galactomannan and the detection method of example 21 with the exception that the fluorescence of the labelled galactomannan remaining in the film was measured.

The results of the comparison is shown in the following table:

| µ/ml BXM 3 | Textile (% change) | Bacterial Cellulose (% change) |
| --- | --- | --- |
| 15.0 | 99.8 | 100 |
| 5.0 | 110.4 | 106.0 |
| 2.5 | 91.5 | 90.3 |
| 1.0 | 51.2 | 66.7 |
| 0.2 | 17.3 | 28.8 |
| 0.0 | 0 | 0 |

The results shows that the change of fluorescence versus concentration of BXM 3 mannanase is similar for both the textile and the cellulose film. Accordingly the removal of substrate from a cellulose film simulates very well the removal of substrate from a textile and that use of a film of MFC in microscale containers may replace textile when detecting enzymes. The standard derivation of the textile and bacterial cellulose film assay is 4–8% and 2–8%, respectively, based on 4 measurements, proving that detecting using a cellulose film is more reproducible.

Example 25

Dual probe assay for enzyme specificity.

This experiment was conducted to show that a cellulose film can be prepared incorporating two different enzyme substrates towards which different enzymes have different specificity. By mixing two different substrates, each labelled with a probe with unique spectral properties, one can use the ratio of the signals to categorize the specificity of an enzyme sample for the two substrates.

To illustrate this concept using cellulases two substrates were prepared: Carboxymethylcellulose labelled with eosin (CMC-E) and bacterial cellulose labelled with fluorescein (BC-F). A film was prepared in micro titer plate wells with a mixture of these two substrates, and the film was incubated with either of two different cellulases: Endoglucanase I or Endoglucanase V from *H.insolens* (both cloned and expressed in A.oryzae as described earlier). These two enzymes are known to have different substrate specificities.

Experimental

BC-F was prepared as described previously.

CMC-E was prepared by the following procedure: 1,005 g CMC was dissolved in 50 mL water and pH was adjusted to 5,9 on 0.1 N NaOH. 48.9 mg 5-aminoeosin dissolved in 2 mL DMF was added. 1.24 g EDAC was added in small portions over 1 h. The reaction mixture was stirred overnight at room temperature. The product was precipitated in a mixture of 15 mL MeOH and 500 mL EtOH. The labelled polymer was washed in EtOH and freeze-dried 10 microliter CMC-E (0,5 mg/ml) was mixed with 100 microliter BC-F (1 mg/ml) in each well of a 96-well plate and incubated at 50° C. overnight to form the dual labelled film.

Solutions of EG I and of EG V at concentrations of 0; 62,5; 125; and 250 mg/L were prepared.

25 microliter enzyme solution and 200 microliter buffer (0,05 M tris, pH 7,6) was incubated in each well for 2 h at 37° C.

25 microliter of the supernatant of each well was taken as samples and was diluted with 200 microliter buffer and the fluorescence intensity at 515/555 nm (for eosin) and 485/520 nm (for fluorescein) was measured using a Polarstar fluorimeter. Each value was corrected for the average fluorescence intensity of the blank samples, and the ratio of the corrected eosin and fluorescein fluorescence intensities was calculated as an indication of the enzyme specificity.

Results

| Conc. (mg/L) | EGI | EGI | EGV | EGV |
|---|---|---|---|---|
| Eosin fluorescence intensity (corrected; arbitrary units) | | | | |
| 0 | | 0 ± 626 | | |
| 62.5 | 1822 | 2436 | 3753 | 3268 |
| 125 | 2489 | 2847 | 4928 | 4382 |
| 250 | 2141 | 2672 | 5406 | 5312 |
| Fluorescein fluorescence intensity (corrected; arbitrary units) | | | | |
| 0 | | 0 ± 65 | | |
| 62.5 | 1450 | 1720 | 6073 | 5666 |
| 125 | 1856 | 2219 | 7180 | 6301 |
| 250 | 2065 | 2897 | 9627 | 9882 |
| Ratio of corrected fluor. intensities (eosin/fluorescein) | | | | |
| 0 | | N.D. | | |
| 62.5 | 0.80 | 0.71 | 1.62 | 1.73 |
| 125 | 0.75 | 0.78 | 1.46 | 1.44 |
| 250 | 0.96 | 1.08 | 1.78 | 1.86 |

It can be seen from the results, that the EGV enzyme in all cases give a much higher E/F ratio, indicating the separate specificity of this enzyme. As EGV and EGI are both commercial enzymes that each have a separate function in detergents, this assay format can be useful to rapidly determine if cellulase enzymes have EGI-like or EGV-like substrate specificity.

Example 26

Use of bacterial cellulose films for assaying protein degradation from solid surfaces Fluorescently labelled haemoglobin was mixed with bacterial cellulose, and a cellulose film was prepared in the wells of polystyrene 96-well microtiter plates. The cellulose films were dried and used in dose-response wash performance experiments with protease. The "stain removal" ability of laundry detergent with Savinase® protease (a conventional detergent protease) was tested.

Labelling of Heamoglobin

Fluorescein-5-isothiocyante 'isomer I' (FITC; Molecular Probes F-143) was covalently coupled to bovine haemoglobin (Sigma H-2625, lot. 125H9310) by dissolving 15.4 g of the protein in 600 ml 0.25 M $NaHCO_3$ pH 9.0, and 156.8 mg FITC in 250 ml 0.25 M $NaHCO_3$ pH 9.0. The two solutions were mixed and stirred in darkness for 60 min at room temperature. Unbound FITC was removed by gel filtration on a 4 1 Sephadex 25 column (Amersham Pharmacia Biotech). The collected 880 ml was supplemented with glycerol to a final concentration of 50% (w/v). 0.1% (w/w) 50% glutaric aldehyde (Merck 814393) was added and the mixture was stirred for 1 h at room temperature.

Bacterial Cellulose

Bacterial cellulose (BC) was obtained from Nata de Coco (Del Monte) by washing the cubes in water followed by 5 overnight washes in 1% NaOH, and 6 overnight washes in water. The cubes were subsequently homogenised in a blender and dialysed against mili Q water (12–14,000 cut-off). The final product was in a concentration of 1 g solids per litre water.

Preparation of Cellulose Film With Labelled Haemoglobin

The prepared FITC-haemoglobin and BC were mixed in ratios Heamoglobin:BC of 1:10, 1:4 and 1:2 and films were prepared by dispensing these mixtures in wells of polystyrene microtiter plates (Nunc 269620). Films were formed by drying the dispensed mixtures overnight at 50° C.

Samples of different concentration of purified Savinase® were prepared in water and dissolved in 6 g/l of a commercial detergent. A total of 165 µl protease in detergent was added per well. The plates were shaken for 30 min at room temperature and 100 µl of the wash supernatants were taken as samples and transferred to black microtiter plates (Sterilin 611F96BK). Fluorescence (excitation at 485 nm, emission at 520 nm) of the supernatants was measured in a spectrofluorometer (BMG Polarstar).

Results

| Fluorescence intensity (arbitrary units) | | | |
|---|---|---|---|
| Heamoglobin:BC | 1:2 | 1:4 | 1:10 |
| µg protease/ml | | | |
| 0 | 20745 | 14848 | 6086 |
| 0.1 | 25687 | 16773 | 6437 |
| 0.25 | 28659 | 20279 | 8210 |
| 0.5 | 32892 | 25093 | 10779 |
| 1 | 35339 | 30037 | 14336 |
| 2 | 38813 | 35370 | 18134 |
| 3 | 42860 | 38996 | 18118 |
| 5 | 47854 | 41867 | 20472 |

At the selected conditions, the fluorescence of the wash supernatants increased with enzyme dosage reflecting increased amounts of released haemoglobin, while the level of fluorescence increased with the increased amount of labelled haemoglobing in the film. The example also show that the performance of an enzyme which works well in a real cleaning application can be evaluated in a test system of the invention using a cellulose film in stead of real textile.

What is claimed is:

1. A method for screening for an active comprising contacting a sample containing the active with a cellulose film comprising microfibrillated cellulose and detecting an interaction between the cellulose film and active.

2. The method of claim 1 further comprising the steps of
   (a) depositing a cellulose film comprising microfibrillated cellulose on at least one inner surface of a container,
   (b) adding the active dissolved or dispersed in a liquid to the film,
   (c) Incubating the film with the active and
   (d) monitoring the interaction between the active and the cellulose film, preferably by measuring a compound which have been released from the film by the interaction.

3. The method of claim 1, wherein the active is selected from the group consisting of biological compounds, inorganic detersive compounds and organic detersive compounds.

4. The method of claim 3, wherein the biological compound is an enzyme.

5. A method for screening for a nucleic acid sequence encoding a biological compound, the method comprising:
   (a) expressing the nucleic acid sequence in an expression system, so as to produce the biological compound, (b) contacting the biological compound with a cellulose film, (c) measuring an interaction between the biological compound and the cellulose film and (d) selecting expression systems for which a detectable interaction occurred and recovering the nucleic acid sequence.

6. The method of claim 5, wherein the expression system is an in vitro coupled translation/transcription system.

7. The method of claim 5, wherein the expression system is a cellular expression system.

8. The method of claim 7, wherein the cellular expression system is a wild type cell.

9. A method for producing a biological compound comprising:

a) contacting a cellulose film with a population of cells or in vitro expression systems comprising a gene library that expresses at least one biological compound of interest, (b) identifying in the population, a cell or in vitro expression system which expresses a biological compound that interacts with the cellulose film;

(c) selecting the cell or In vitro expression system producing the biological compound, (d) identifying a nucleic acid sequence encoding the biological compound, (e) cultivating a cell comprising a nucleic acid sequence encoding the biological compound so as to produce the biological compound and, (f) recovering the biological compound.

10. A modified cellulose film comprising microfibrillated cellulose, wherein the film further comprises a substance attached to the cellulose film.

11. The cellulose film of claim 10, wherein the substance is attached to the cellulose film by covalent bonds, by ionic bonds or by hydrogen bonds.

12. The cellulose film of claim 11, wherein the substance is attached onto the surface of the film after formation of the film.

13. The cellulose film of claim 10, wherein the compound is selected from the group consisting of a dye, a radioactive compound, a non cellulose substrate and non-microfibrillated cellulose substrate.

14. The cellulose film of claims 13, wherein the dye is selected from the group consisting of light absorbing dyes and fluorescent dyes.

15. The cellulose film of claims 14, wherein the dye is a fluorescent dye.

16. The cellulose film of claims 13, wherein the radioactive compound comprises an isotope selected from the group consisting of S35, P32, H3 and I125.

17. A method preparing a cellulose film of claim 10 comprising preparing a suspension of microfibrillated cellulose, sedimenting the microfibrillated cellulose as a film onto a surface and contacting the microfibrillated cellulose with a substance before, during or after the formation of the film.

18. A test container for biological screening comprising at least one surface coated with a cellulose film.

19. The method according to claim 10, wherein the cellulose film comprises a substance attached to the cellulose film and the biological compound interacts with the substance.

* * * * *